US010517846B2

(12) United States Patent
Pawar et al.

(10) Patent No.: US 10,517,846 B2
(45) Date of Patent: Dec. 31, 2019

(54) PHARMACEUTICAL COMPOSITIONS FOR TREATING ACNE

(71) Applicant: Dr. Reddy's Laboratories Ltd., Hyderabad, Telangana (IN)

(72) Inventors: Yogesh Bapurao Pawar, Maharashtra (IN); Kailas Khomane, Hyderabad (IN); Saurabh Srivastava, Allahabad (IN); Bijay Kumar Padhi, Odisha (IN); Rajeev Singh Raghuvanshi, Gurgaon (IN)

(73) Assignee: DR. REDDY'S LABORATORIES LTD., Hyderbad, Telangana (IN)

( * ) Notice: Subject to any disclaimer, the term of this patent is extended or adjusted under 35 U.S.C. 154(b) by 0 days.

(21) Appl. No.: 15/607,125

(22) Filed: May 26, 2017

(65) Prior Publication Data
US 2017/0340594 A1 Nov. 30, 2017

(30) Foreign Application Priority Data

May 26, 2016 (IN) .............................. 201641006784

(51) Int. Cl.
*A61K 31/203* (2006.01)
*A61K 9/48* (2006.01)
*A61K 9/50* (2006.01)
*A61K 9/00* (2006.01)
*A61K 9/14* (2006.01)
*A61K 9/20* (2006.01)
*A61K 47/12* (2006.01)
*A61K 47/32* (2006.01)

(52) U.S. Cl.
CPC .......... *A61K 31/203* (2013.01); *A61K 9/0002* (2013.01); *A61K 9/146* (2013.01); *A61K 9/2022* (2013.01); *A61K 47/12* (2013.01); *A61K 47/32* (2013.01)

(58) Field of Classification Search
CPC ...... A61K 31/203; A61K 47/12; A61K 47/32; A61K 9/0002; A61K 9/146; A61K 9/2022; A61K 9/4808; A61K 9/5026; A61K 9/5042; A61K 9/5047
See application file for complete search history.

(56) References Cited

U.S. PATENT DOCUMENTS

| | | | |
|---|---|---|---|
| 6,764,698 B1 | 7/2004 | Byun et al. | |
| 7,435,427 B2 | 10/2008 | Vanderbist et al. | |
| 8,293,277 B2 * | 10/2012 | Swanson ................ | A61K 9/146 424/464 |
| 8,367,102 B2 | 2/2013 | Vanderbist et al. | |
| 8,952,064 B2 | 2/2015 | Vanderbist et al. | |
| 9,078,925 B2 | 7/2015 | Deboeck et al. | |
| 9,089,534 B2 | 7/2015 | Vanderbist et al. | |
| 9,700,535 B2 | 7/2017 | Rao et al. | |
| 9,750,711 B2 | 9/2017 | Madan et al. | |
| 2003/0215496 A1 * | 11/2003 | Patel .................... | A61K 9/1617 424/452 |
| 2009/0011009 A1 | 1/2009 | Benita et al. | |
| 2016/0081964 A1 * | 3/2016 | Rao .......................... | A61K 9/16 424/455 |
| 2017/0258748 A1 | 9/2017 | Rao et al. | |
| 2017/0326091 A1 | 11/2017 | Madan et al. | |
| 2017/0326092 A1 | 11/2017 | Venkateshwaran et al. | |

FOREIGN PATENT DOCUMENTS

| | | |
|---|---|---|
| EP | 0357646 A1 | 3/1990 |
| IN | 249181 | 10/2011 |
| WO | WO 00/00179 * | 1/2000 |
| WO | 2015/181802 A2 | 12/2015 |
| WO | 2015/186039 A1 | 12/2015 |
| WO | 2016/016742 A1 | 2/2016 |
| WO | 2016/051288 A1 | 4/2016 |
| WO | 2016/189481 A1 | 12/2016 |
| WO | 2016/193779 A1 | 12/2016 |

OTHER PUBLICATIONS

Tadini (Pharmazie, 61, 5, 2006.*
Gao (Molecular Pharmaceutics, 2008, p. 903-904) (Year: 2008).*
Strauss, J.S., et al. "A randomized trial of the efficacy of a new micronized formulation versus a standard formulation of isotretinoin in patients with severe recalcitrant nodular acne", J Am Acad Dermatol, Aug. 2001, vol. 45, No. 2, p. 187-195.

* cited by examiner

*Primary Examiner* — Umamaheswari Ramachandran
(74) *Attorney, Agent, or Firm* — Stites & Harbison, PLLC; Mandy Wilson Decker; Sean P. Ritchie

(57) ABSTRACT

The present application relates to pharmaceutical compositions comprising retinoic acid or its derivatives such as isotretinoin and processes for preparing thereof. It also provides methods for treating acne by administering such pharmaceutical composition to a patient in need thereof.

31 Claims, 10 Drawing Sheets

FIGURE 1

PHARMACEUTICAL COMPOSITIONS FOR TREATING ACNE

RELATED APPLICATIONS

This application claims priority from Indian Provisional Application No. IN 201641006784, filed on May 26, 2016, the entire disclosure of which is incorporated herein by this reference.

TECHNICAL FIELD

The present application relates to a pharmaceutical composition comprising retinoic acid or its derivatives such as isotretinoin and processes for preparing thereof. It also provides methods for treating acne by administering such pharmaceutical composition to a patient in need thereof.

BACKGROUND

Acne is a disease of the skin in which the pilosebaceous structures of the skin become inflamed, leading to the formation of comedones, pustules, and nodules. It is generally believed that acne arises when hyperkeratosis of the pilosebaceous structure wholly or partially blocks the opening of the structures, resulting in comedones filled with sebum, keratin, and *Propionibacterium acnes* ("*P. acnes*"). These lesions are commonly identified as acne. *P. acnes* naturally occur in normal skin but is especially and characteristically present in acne lesions. Acne naturally varies in severity from mild to very severe. People with severe (deep, or cystic) acne, on the other side, have numerous large, red, painful pus-filled lumps (nodules) that sometimes even join together under the skin into giant, oozing abscesses. Depending on the degree of severity and pronounced appearance, acne can be acne vulgaris, acne comedonica, acne papulo pustulosa, acne conglobata, etc. which are, inflammatory acne or non-inflammatory acne.

Conventional acne treatments have a varied range of alternatives available which includes, topical therapy using benzoyl peroxide, keratolytic agents like salicylic acid; local or systemic treatments using antibiotics like tetracycline, minocycline, doxycycline, clindamycin, erythromycin, azithromycin, macrolides, co-trimoxazole, and trimethoprim or using retinoids like tretinoin, adapalene, tazarotene, isotretinoin, metretinide, retinaldehyde, and β-retinoyl glucuronide; hormonal therapy—to prevent the effects of androgens on the sebaceous gland using norgestimate with ethinyl estradiol, and norethindrone acetate with ethinyl estradiol; various physical treatments and the like or combinations thereof. Suitable treatment option can be decided considering severity of acne and therapeutic effect of available drug, for example, oral antibiotics are indicated mainly in moderate-to-severe inflammatory acne whereas oral retinoids are preferred in case of severe, scarring and/or refractory acne.

While a variety of acne treatments do exist, retinoids have been widely described for treatment of a number of dermatological disorders, including both acne and seborrhoea. The available topical dosage forms have been reported to produce skin irritation (dermatitis) that may include erythema, scaling, peeling, drying, pruritus, and sensations similar to sunburn. Oral retinoids are indicated in severe, moderate-to-severe acne or lesser degree of acne producing physical or psychological scarring, unresponsive to adequate conventional therapy. Orally administered retinoic acid—13-cis retinoic acid (isotretinoin) revolutionized the treatment of severe forms of acne when it was introduced in 1982, and continues to be a widely used single therapy for treating severe acne. Oral isotretinoin is so effective against acne because it is the only treatment affecting all major etiological factors, including, in particular, a substantial reduction of sebum production by inhibition of the lipogenesis, as well as a reduction of the size of sebaceous glands of the patient. Thus, it is established as the gold standard of acne therapy, capable of long-term remission in about 80% of patients with severe acne.

At present, oral retinoic acid is available as various capsules with options to choose from with food or without food. Retinoic acid like isotretinoin is a synthetic retinoic acid derivative, also known as 13-cis retinoic acid, which is chemically (2Z,4E,6E,8E)-3,7-dimethyl-9-(2,6,6-trimethyl-cyclohex-1-en-1-yl)nona-2,4,6,8-tetraenoic acid. It has very low water solubility and thus has formulating challenges to provide oral dosage forms. There are few arts which describes oral formulations of isotretinoin. For example, WO 2000/025772, WO 2015/181802, WO 2015/186039 A1, WO 2016/016742 A1, WO 2016/051288 A1, WO 2016/189481 A1, WO 2016/193779 A1, U.S. Pat. Nos. 6,740,337, 7,435,427 and 8,367,102 relate to micronized isotretinoin present as dispersion, suspension or semi-solid suspension formulated for oral administration, which may also include oily vehicle; IN 249181 discloses isotretinoin tablets prepared with fumaric acid.

Commercially available oral isotretinoin formulations comprise an oil/lipid based vehicle. Retinoids have side effects of developing high levels of cholesterol and other fats in the blood among other known teratogenic effects. The use of oil/lipid based formulations may further increases chances of such adverse events. As such, there remains an unmet need in the art for oral formulations of retinoic acid, free of such oily/lipidic vehicles, which can also provide efficient dosing without regard to food effect/reduced food effect. Additionally, considering teratogenic nature of retinoic acids, there is also a continuing need to provide once-daily doses, as opposed to the currently prescribed divided daily doses.

SUMMARY OF THE APPLICATION

The present application provides retinoic acid compositions, like isotretinoin compositions for the treatment of acne comprising solubilized drug using a simple vehicle system, which are completely bioavailable, have significantly reduced food effect, and can also be suitable for administering once daily or twice daily.

In an embodiment, the present application relates to a pharmaceutical composition comprising isotretinoin or a pharmaceutically acceptable salt thereof, wherein at least 60% of said isotretinoin is in an amorphous form.

In another embodiment, the present application relates to a once daily pharmaceutical composition comprising isotretinoin or a pharmaceutically acceptable salt thereof, wherein at least 60% of said isotretinoin is in an amorphous form.

In another embodiment, the present application relates to a pharmaceutical composition comprising isotretinoin or a pharmaceutically acceptable salt thereof, wherein at least 60% of said isotretinoin is in an amorphous form; and wherein said composition is substantially free of isotretinoin particles.

In an embodiment, the present application relates to a pharmaceutical composition of isotretinoin comprising:

(i) isotretinoin or a pharmaceutically acceptable salt thereof,
(ii) at least one solubility improving polymer; and
(iii) at least one rate controlling agent, wherein at least 60% of said isotretinoin is in an amorphous form.

In another embodiment, the present application relates to a pharmaceutical composition of isotretinoin comprising:
(i) isotretinoin or a pharmaceutically acceptable salt thereof,
(ii) at least one solubility improving polymer; and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours.

In yet another embodiment, the present application relates to a once daily pharmaceutical composition of isotretinoin comprising:
(i) isotretinoin or a pharmaceutically acceptable salt thereof,
(ii) at least one solubility improving polymer; and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours;
wherein at least 60% of said isotretinoin is in an amorphous form.

In yet another embodiment, the present application relates to a pharmaceutical composition of isotretinoin comprising:
(i) isotretinoin or a pharmaceutically acceptable salt thereof, and
(ii) at least one solubility improving polymer selected from ionizable polymer, non-ionizable polymer, and mixtures thereof,
wherein at least 60% of said isotretinoin is in an amorphous form.

In yet another embodiment, the present application relates to a once daily pharmaceutical composition of isotretinoin comprising:
(i) isotretinoin or a pharmaceutically acceptable salt thereof,
(ii) at least one solubility improving polymer selected from ionizable polymer, and
(iii) at least one rate controlling agent,
wherein at least 60% of said isotretinoin is in an amorphous form.

In yet another embodiment, the present application relates to a once daily pharmaceutical composition of isotretinoin comprising:
(i) isotretinoin or a pharmaceutically acceptable salt thereof,
(i) at least one solubility improving polymer selected from non-ionizable polymer, and
(iii) at least one rate controlling agent,
wherein at least 60% of said isotretinoin is in an amorphous form.

In an aspect of the above embodiments, the pharmaceutical composition of the present application further comprises at least one wetting agent.

In an embodiment, the present application relates to a once daily pharmaceutical composition of isotretinoin comprising:
(i) isotretinoin or a pharmaceutically acceptable salt thereof,
(ii) at least one solubility improving polymer,
(iii) at least one rate controlling agent, and
(iv) at least one wetting agent,
wherein at least 60% of said isotretinoin is in an amorphous form.

In an embodiment, the present application relates to a once daily pharmaceutical composition of isotretinoin comprising:
(i) isotretinoin or a pharmaceutically acceptable salt thereof,
(ii) at least one solubility improving polymer,
(iii) at least one rate controlling agent, and
(iv) at least one wetting agent,
wherein said composition exhibits at least one of the following dissolution profiles when measured in USP type I apparatus at 100 rpm in 900 ml of borate buffer with a pH of 8.0 at 37° C.:
(a) about 1% to about 10% of retinoic acid in 1 hour,
(b) about 10% to about 25% of retinoic acid in 2 hours,
(c) about 25% to about 45% of retinoic acid in 4 hours,
(d) about 45% to about 60% of retinoic acid in 6 hours, and
(e) about 60% to about 80% of retinoic acid in 12 hours.

In an aspect of the above embodiments, the pharmaceutical composition of the present application comprises at least one solubility improving polymer and isotretinoin present in a weight ratio of not more than about 3.0:1.0.

In another aspect of the above embodiments, the pharmaceutical composition of the present application comprises at least one solubility improving polymer and isotretinoin present in a weight ratio of from about 2.0:1.0 to about 3.0:1.0.

In yet another aspect of the above embodiments, the pharmaceutical composition of the present application comprises at least one solubility improving polymer and isotretinoin present in a weight ratio of about 3.0:1.0, about 2.9:1.0, about 2.7:1.0, about 2.5:1.0, about 2.3:1.0, about 2.1:1.0 or about 2.0:1.0.

In an aspect of the above embodiments, the pharmaceutical composition of the present application comprises at least one solubility improving polymer and at least one wetting agent present in a weight ratio of not more than about 10.0:1.0.

In another aspect of the above embodiments, the pharmaceutical composition of the present application comprises at least one solubility improving polymer and at least one wetting agent present in a weight ratio of from about 10.0:1.0 to about 1.0:1.0.

In yet another aspect of the above embodiments, the pharmaceutical composition of the present application comprises at least one solubility improving polymer and at least one wetting agent present in a weight ratio of about 10.0:1.0, about 9.0:1.0, about 8.0:1.0, about 7.0:1.0, about 6.0:1.0, about 5.0:1.0, about 4.0:1.0, about 3.5:1.0, about 3.0:1.0, about 2.5:1.0, about 2.0:1.0, about 1.5:1.0 or about 1.0:1.0.

In an aspect of the above embodiments, the solubility improving polymers of the present application are selected from the group comprising of ionizable polymer, non-ionizable polymer, and mixtures thereof. In some embodiments, the solubility improving polymers comprise from about 10% w/w to about 40% w/w of the composition.

Suitable rate controlling agents that may be used in the present application are selected from the group comprising of pH independent polymers, pH dependent polymers, and mixtures comprising one or more of the foregoing materials.

In some embodiments, the rate controlling agents comprise from about 5% w/w to about 20% w/w of the composition.

The amount of wetting agents used in the present application may range from about 1% w/w to about 15% w/w of the composition.

In an embodiment, the present application relates to a pharmaceutical composition comprising isotretinoin or a pharmaceutically acceptable salt thereof, at least one solubility improving polymer, and one or more pharmaceutically acceptable excipients, wherein said composition comprises isotretinoin in (i) an extended release (ER) portion and (ii) a delayed release (DR) portion and/or an immediate release (IR) portion; and wherein at least 60% of said isotretinoin is in an amorphous form. In some embodiments, the one or more pharmaceutically acceptable excipient is present in the ER portion, the DR portion, and/or the IR portion. Additionally or alternatively, the one or more pharmaceutically acceptable excipient is separate from the ER portion, the DR portion, and/or the IR portion.

In another embodiment, the present application relates to a pharmaceutical composition comprising isotretinoin or a pharmaceutically acceptable salt thereof, and at least one solubility improving polymer, wherein said composition comprises (i) about 60 to about 80 percent of isotretinoin in an extended release (ER) portion, (ii) about 40 to about 20 percent of isotretinoin in a delayed release (DR) portion and/or an immediate release (IR) portion; and (iii) one or more pharmaceutically acceptable excipients; and wherein at least 60% of said isotretinoin is in an amorphous form.

In an embodiment, present application relates to a once daily pharmaceutical composition of isotretinoin comprising,
(i) isotretinoin or a pharmaceutically acceptable salt thereof,
(ii) at least one solubility improving polymer, and
(iii) at least one rate controlling agent,
wherein said composition comprises (i) about 60 to about 80 percent of isotretinoin in an extended (ER) portion; (ii) about 40 to about 20 percent of isotretinoin in a delayed release (DR) portion and/or an immediate release (IR) portion; and (iii) one or more pharmaceutically acceptable excipients; and said composition exhibits at least one of the following dissolution profiles when measured in USP type I apparatus at 100 rpm in 900 ml of borate buffer with a pH of 8.0 and at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours.

In an aspect of the above embodiments, the pharmaceutical composition of the present application is administered orally.

In an aspect of the above embodiments, the pharmaceutical composition of the present application is administered orally, as once-daily.

In an embodiment, the present application relates to a method of treating acne in a patient in need thereof comprising orally administering to the patient a once daily pharmaceutical composition comprising isotretinoin or a pharmaceutically acceptable salt thereof, wherein at least 60% of said isotretinoin is in an amorphous form.

In another embodiment, the present application relates to a method of treating acne in a patient in need thereof comprising orally administering to the patient a once daily pharmaceutical composition of isotretinoin comprising:
(i) isotretinoin or a pharmaceutically acceptable salt thereof,
(ii) at least one solubility improving polymer, and
(iii) at least one rate controlling agent,
wherein at least 60% of said isotretinoin is in an amorphous form.

In another embodiment, the present application relates to a method of treating acne in a patient in need thereof comprising orally administering to the patient a once daily pharmaceutical composition of isotretinoin comprising:
(i) a daily dose of isotretinoin or a pharmaceutically acceptable salt thereof,
(ii) at least one solubility enhancing polymer, and
(iii) at least one rate controlling agent;
wherein said composition upon administration to the patient exhibits plasma level differences for $AUC_{0-24}$ compared to commercially available twice daily isotretinoin composition that provides the same daily dose.

In yet another embodiment, the present application relates to a method of treating acne in a patient in need thereof comprising orally administering to the patient a once daily pharmaceutical composition of isotretinoin comprising:
(i) a daily dose of isotretinoin or a pharmaceutically acceptable salt thereof,
(ii) at least one solubility enhancing polymer, and
(iii) at least one rate controlling agent;
wherein said composition upon administration to the patient exhibits at least one of the following plasma level differences for $AUC_{0-24}$ compared to commercially available twice daily isotretinoin composition that provides the same daily dose:
(a) about 5 to about 10% lower between 0 to 5 hours,
(b) about 15 to about 20% higher between 5 to 14 hours; and
(c) about 4 to about 8% lower between 14 to 24 hours.

In an embodiment, the present application relates to a method of treating acne in a patient in need thereof comprising orally administering to the patient a pharmaceutical composition comprising isotretinoin or a pharmaceutically acceptable salt thereof equivalent to 40 mg of isotretinoin, wherein said composition when administered once daily to said patient under fasting condition, exhibits at least one of the following pharmacokinetic parameters: (a) a $C_{max}$ of about 350.00 ng/ml to about 600.00 ng/ml, (b) an $AUC_{(0-t)}$ of about 5500.00 ng·hr/ml to about 7700.00 ng·hr/ml, and (c) an $AUC_{(0-\infty)}$ ranging from about 5600.00 ng·hr/ml to about 7900.00 ng·hr/ml.

In an embodiment, the present application relates to a method of treating acne in a patient in need thereof comprising orally administering to the patient a pharmaceutical composition comprising isotretinoin or a pharmaceutically acceptable salt thereof equivalent to 40 mg of isotretinoin, wherein said composition when administered once daily to said patient under fed condition, exhibits at least one of the following pharmacokinetic parameters: (a) a $C_{max}$ of about 350.00 ng/ml to about 600.00 ng/ml, (b) an $AUC_{(0-t)}$ of about 6000.00 ng·hr/ml to about 8700.00 ng·hr/ml, and (c) an $AUC_{(0-\infty)}$ ranging from about 6500.00 ng·hr/ml to about 9500.00 ng·hr/ml.

In another embodiment, the present application relates to a method of treating acne in a patient in need thereof comprising orally administering to the patient a pharmaceutical composition comprising isotretinoin or a pharmaceutically acceptable salt thereof, wherein said composition exhibits at least about 10% less food effect compared to commercially available twice daily isotretinoin composition.

In an embodiment, the present application relates to a method of treating acne in a patient in need thereof comprising orally administering to the patient a once daily pharmaceutical composition comprising isotretinoin or a pharmaceutically acceptable salt thereof, wherein at least 60% of said isotretinoin is in an amorphous form.

In an aspect of the above embodiments, the pharmaceutical composition of the present application comprising isotretinoin or a pharmaceutically acceptable salt thereof comprises at least about 60% of said isotretinoin in an amorphous form, wherein at least about 40% of said isotretinoin is in crystalline form.

In an aspect of the above embodiments, a pharmaceutical composition of the present application comprises solid oral dosage forms selected from powder, granules, pellets, mini-tablets, tablets, capsules or caplets.

In another aspect of the above embodiments, the pharmaceutical composition of the present application is stable and provides chemical and physical stability of isotretinoin in said composition wherein there is no precipitation and no change in assay values, drug release and composition characteristics such as impurities, drug concentration, appearance and the like as disclosed herein, when kept at 40° C./75% RH and at 25° C./60% RH for 3 to 6 months.

In another aspect of the above embodiments, the pharmaceutical composition of the present application is stable and provides chemical and physical stability of isotretinoin in said composition wherein there is no precipitation and no change in assay values, drug release and composition characteristics such as impurities, drug concentration, appearance and the like as disclosed herein, when kept at 40° C./75% RH and at 25° C./60% RH for at least 3 months.

In another aspect of the above embodiments, the pharmaceutical composition of the present application is stable and provides chemical and physical stability of isotretinoin in said composition wherein there is no precipitation and no change in assay values, drug release and composition characteristics such as impurities, drug concentration, appearance and the like as disclosed herein, when kept at 40° C./75% RH and at 25° C./60% RH for at least 6 months.

BRIEF DESCRIPTION OF THE DRAWING

Figure 1:
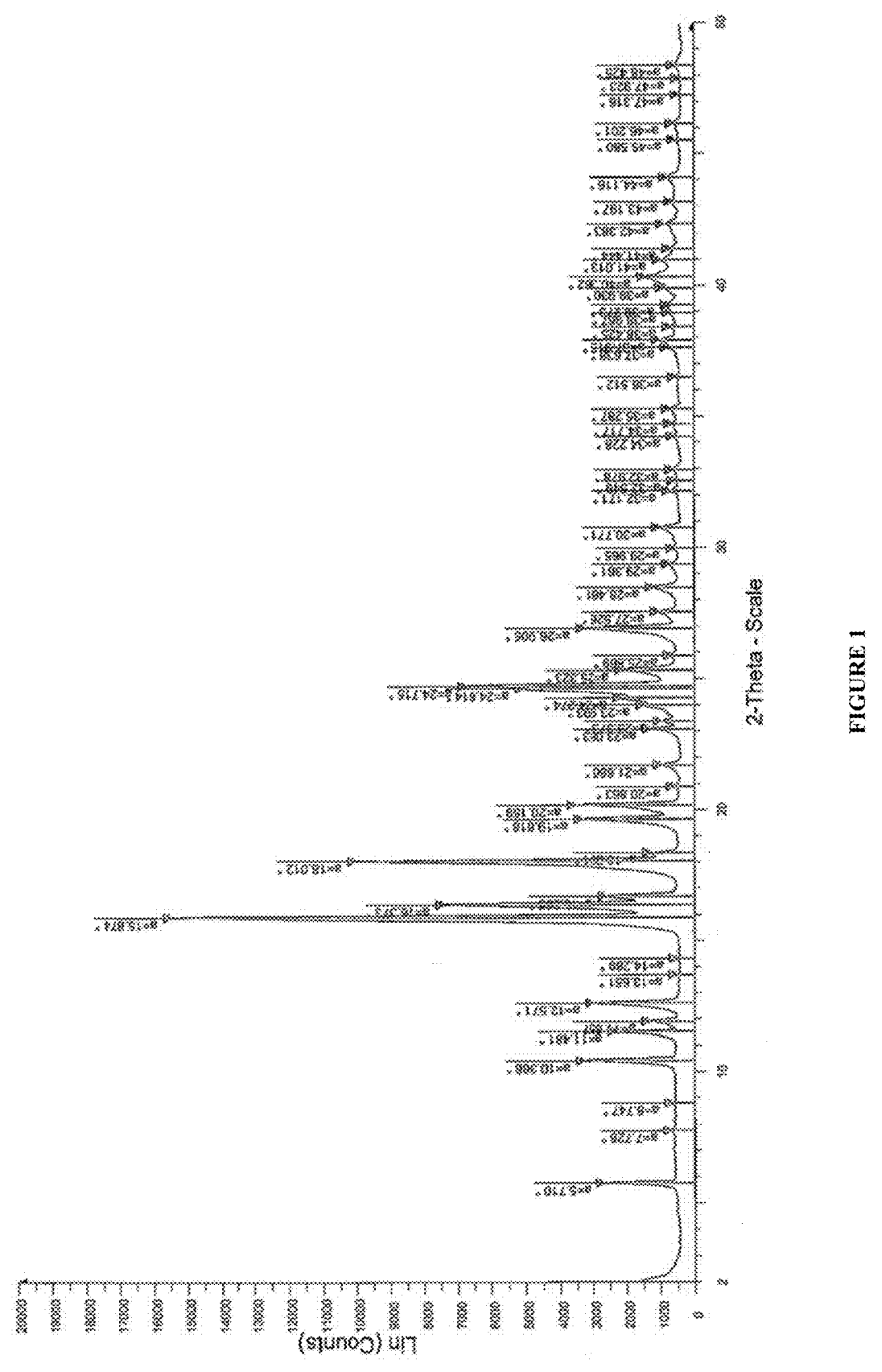

FIG. 1 shows Powder X-Ray Diffraction (PXRD) patterns of API—isotretinoin crystalline form.

DETAILED DESCRIPTION OF THE EMBODIMENTS

Figure 2A:
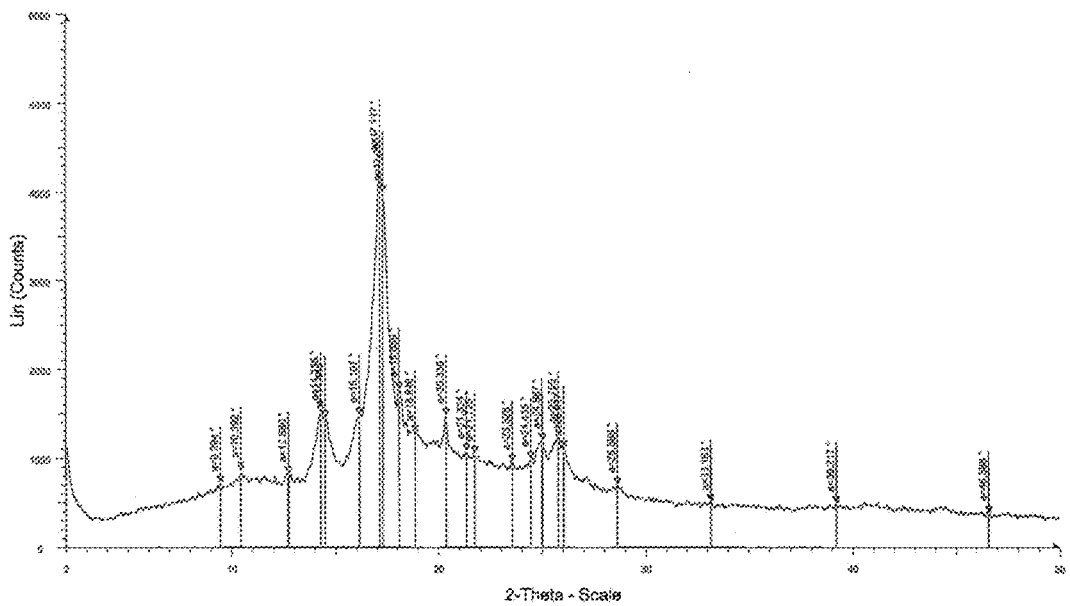
FIGS. 2A-B show Powder X-Ray Diffraction (PXRD) patterns of (A) Polymer A (Hypromellose acetate succinate) active film with isotretinoin; and (B) Polymer A placebo film.
Figure 2B:
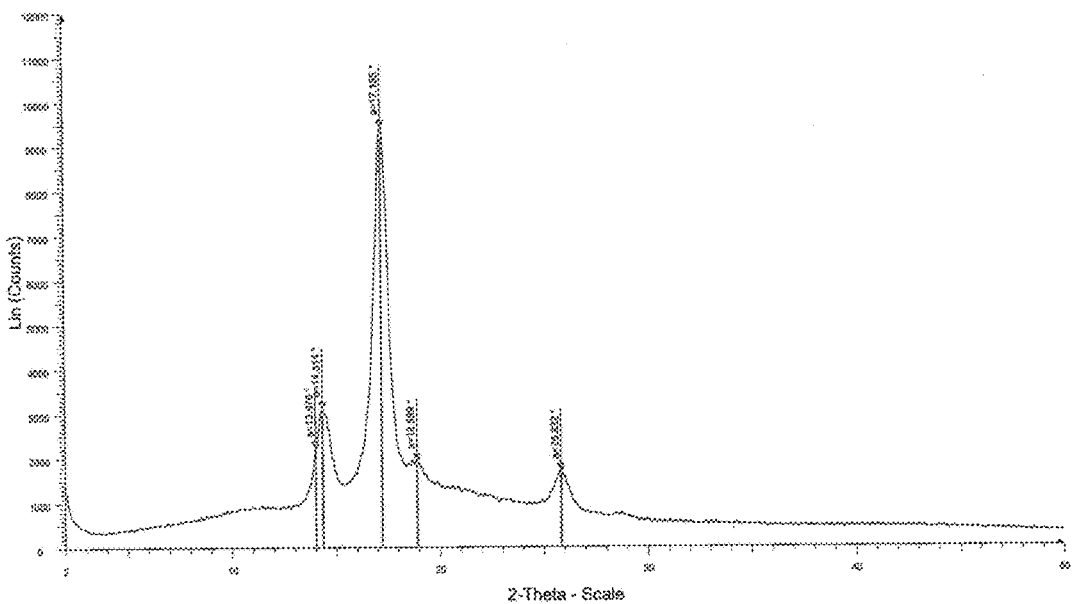
Figure 3A:
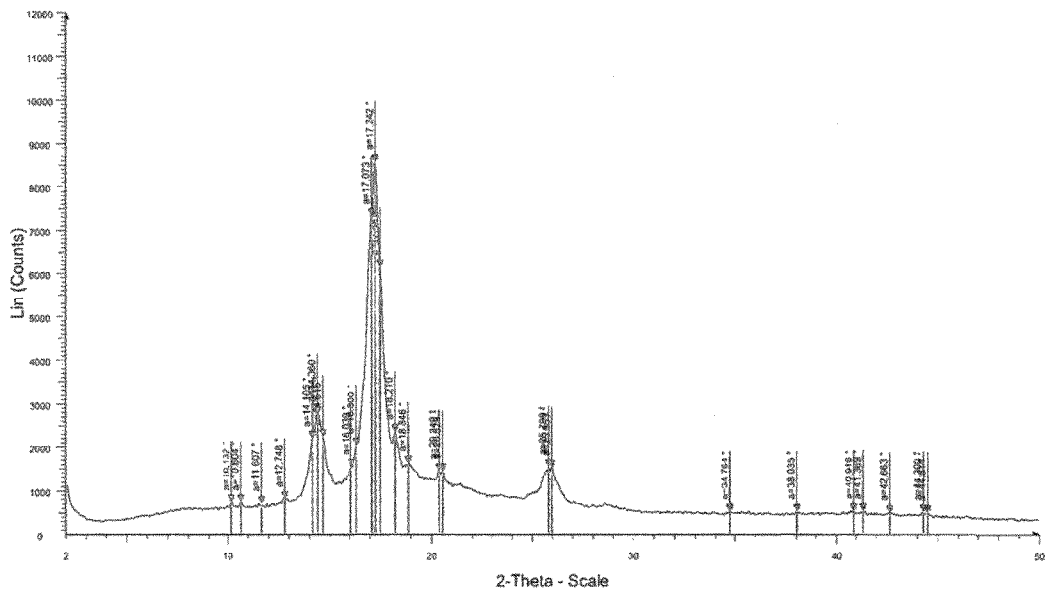
FIGS. 3A-B show Powder X-Ray Diffraction (PXRD) patterns of (A) Polymer B (Hydroxypropyl methyl cellulose) active film with isotretinoin; and (B) Polymer B placebo film.
Figure 3B:
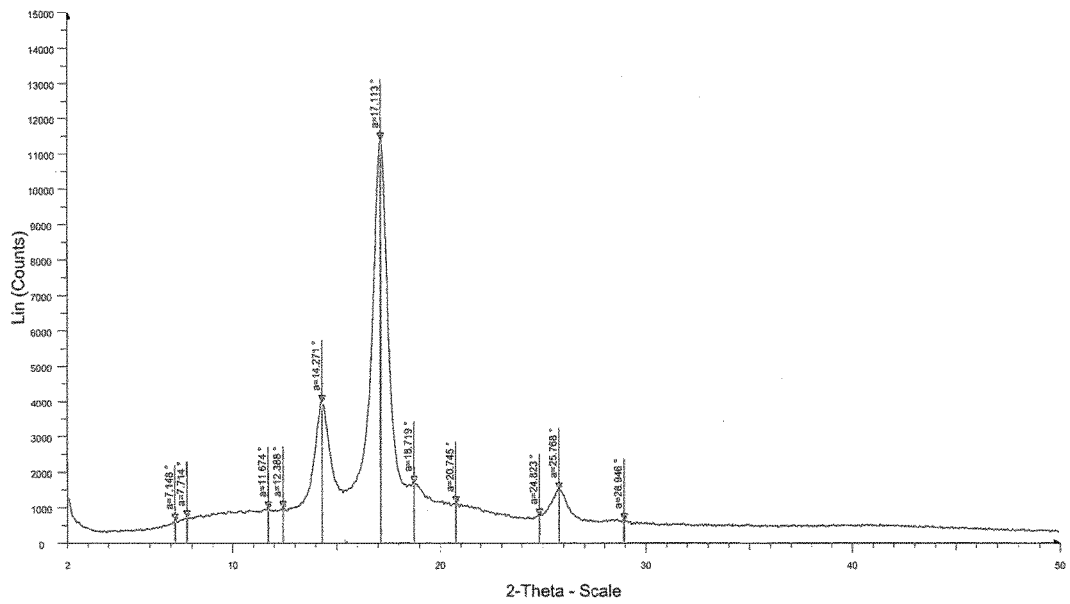
Figure 4A:
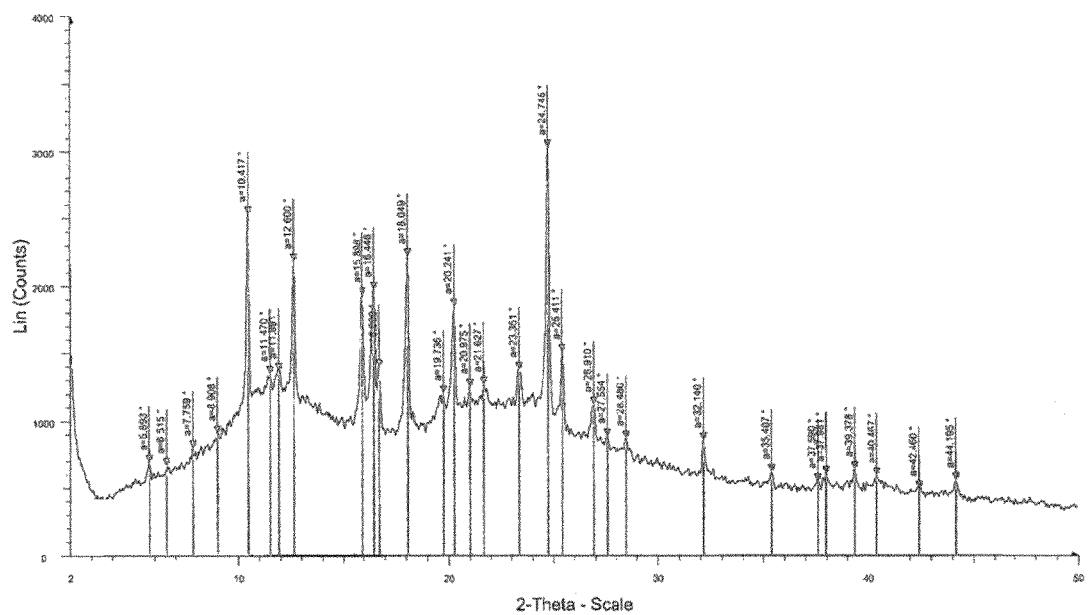
FIGS. 4A-B show Powder X-Ray Diffraction (PXRD) patterns of (A) Polymer C (Copolymer of 1-vinyl-2-pyrrolidone and vinyl acetate—Kollidon® VA 64) active film with isotretinoin; and (B) Polymer C placebo film.
Figure 4B:
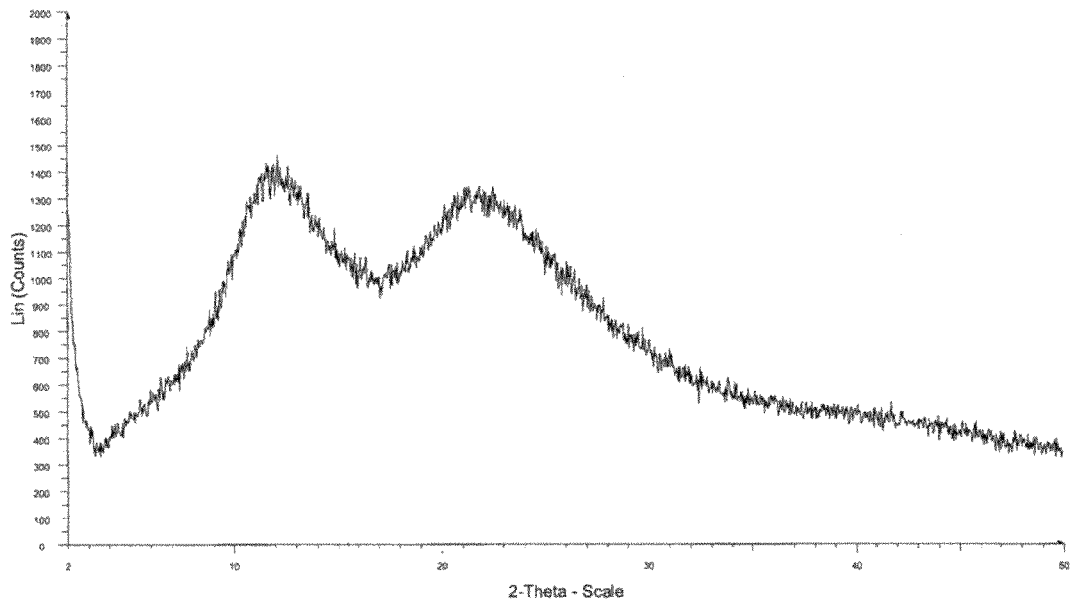
Figure 5A:
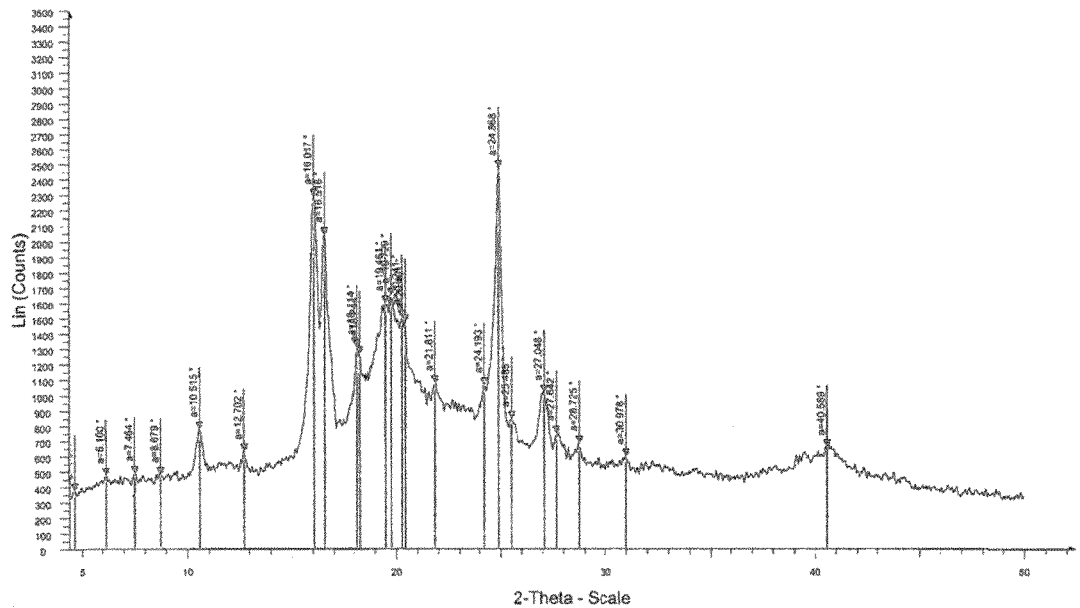
FIGS. 5A-B show Powder X-Ray Diffraction (PXRD) patterns of (A) Polymer D (Polyvinyl alcohol) active film with isotretinoin; and (B) Polymer D placebo film
Figure 5B:
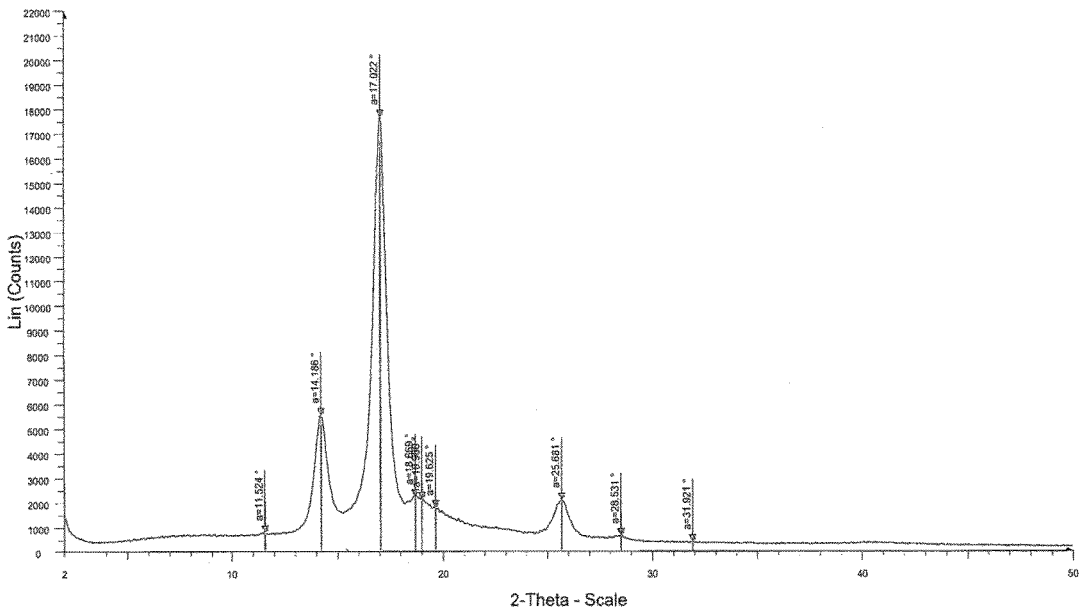
Figure 6A:
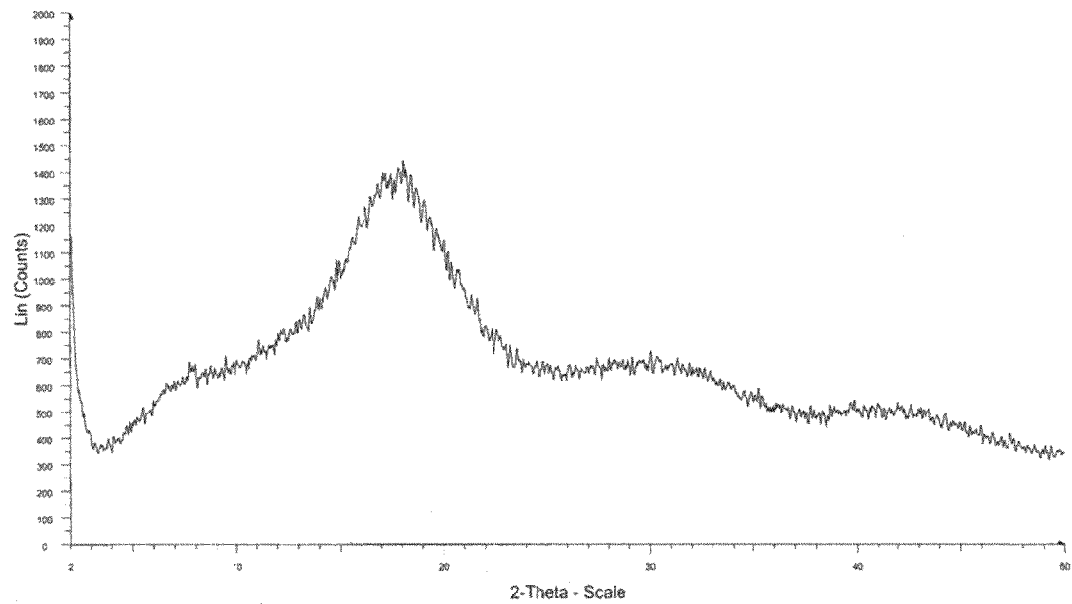
FIGS. 6A-B show Powder X-Ray Diffraction (PXRD) patterns of (A) Polymer E (Dimethyl aminoethyl methacrylate—butyl methacrylate—methyl methacrylate copolymer—Eudragit® E PO) active film with isotretinoin; and (B) Polymer E placebo film.
Figure 6B:
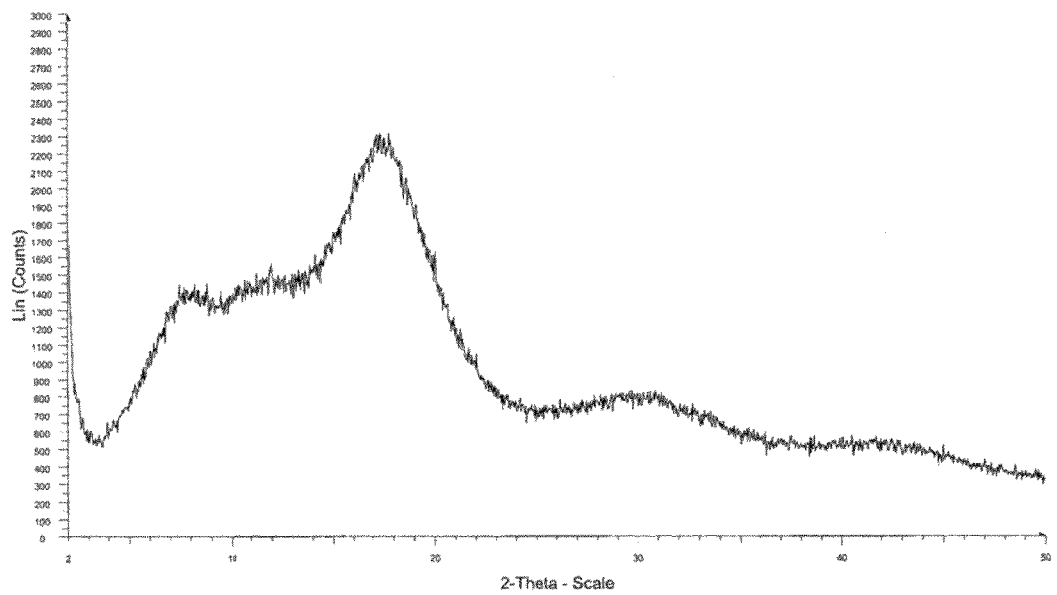
Figure 7A:
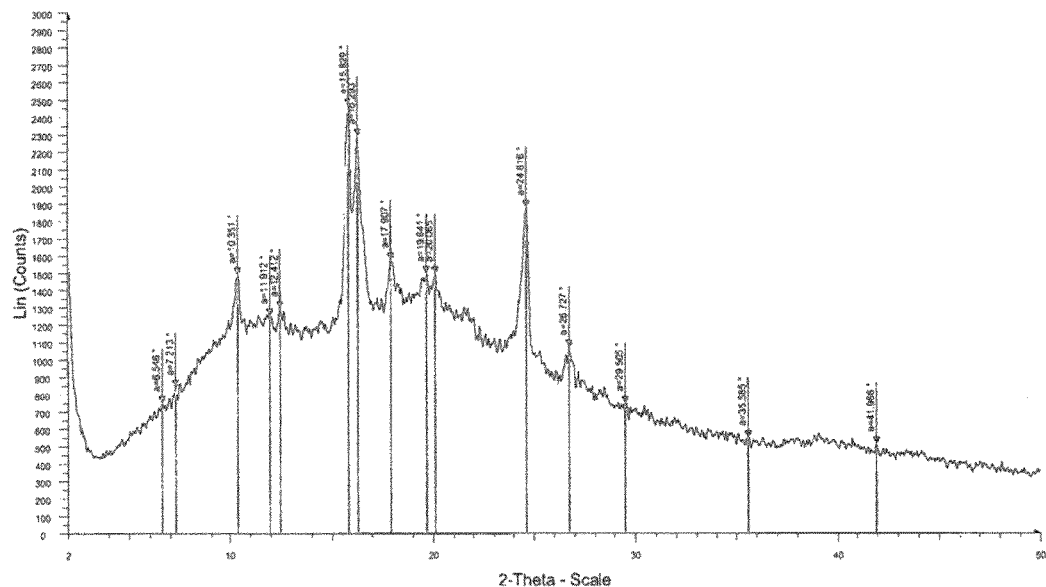
FIGS. 7A-B show Powder X-Ray Diffraction (PXRD) patterns of (A) Polymer F (Polyethylene glycol-polyvinyl acetate-polyvinyl caprolactame based graft copolymer—Soluplus®) active film with isotretinoin; and (B) Polymer F placebo film.
Figure 7B:
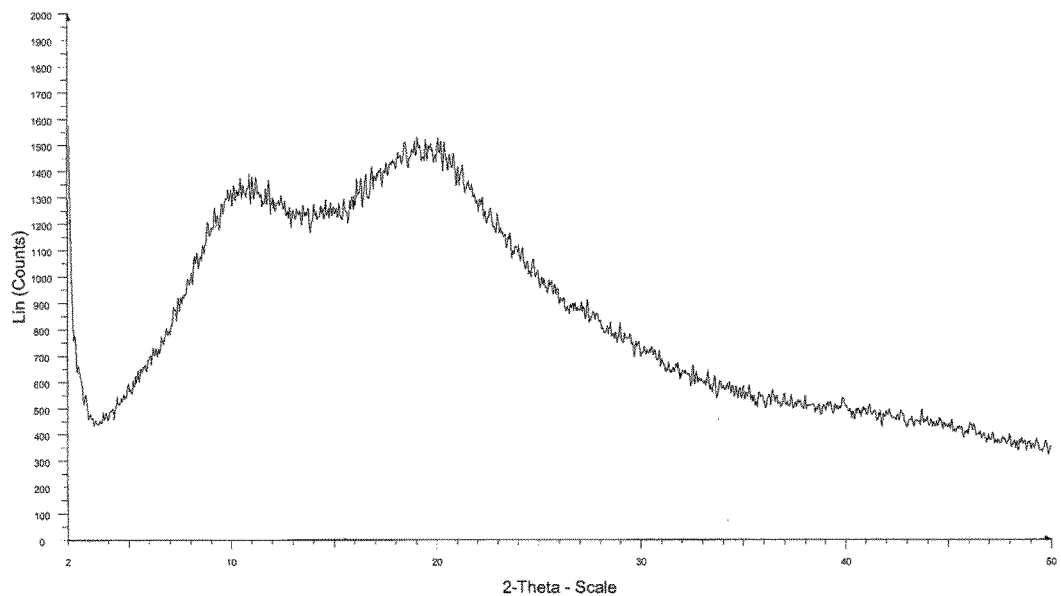

The details of one or more embodiments of the present application are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Definitions

The terms as used herein have the following meanings:

The term "comprising" means the elements recited, or their equivalent in structure or function, plus any other element or elements which are not recited. The terms "having" and "including" are also to be construed as open ended unless the context suggests otherwise. All ranges recited herein include the endpoints, including those that recite a range "between" two values.

The terms "a" and "the" as used herein are understood to encompass the plural as well as the singular or otherwise clearly mentioned wherever needed. For example, reference to "an excipient" includes reference to one or more of such excipients, and reference to "the vehicle" includes reference to one or more of such vehicles.

The terms such as "about," "up to," "generally" and the like are to be construed as modifying a term or value such that it is not an absolute. Such terms will be defined by the circumstances, and the terms that they modify as those terms are understood by those of skill in the art. This includes, at very least, the degree of expected experimental error, technical error and instrumental error for a given experiment, technique or an instrument used to measure a value. The term "about," as used herein, means within 10% of a given value or range. The term "about" also used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Alternatively, the term "about" means within an acceptable standard error of the mean.

As used herein, the term "at least" refers to presence of recited substance in the composition in recited least amount.

As used herein, the terms "composition" and "formulation" are used interchangeably and refer to a mixture of two or more compounds, elements, or molecules. Also, the terms "composition" and "formulation" may be used to refer to a mixture of one or more active agents with excipients or other carriers. Furthermore, the term "dosage form" can include one or more composition(s) or formulation(s) provided in a format for administration to a subject like powder, granules, pellets, mini-tablets, tablets, capsules, caplets, and the like.

As used herein, the "daily dose" or "once daily dose" refers to a composition formulated to provide a desired amount of a drug with a once a day administration thereof. For example, a "daily dose" or "once daily dose" of isotretinoin or a pharmaceutically acceptable salt thereof means a once daily administration of a composition to a patient in need thereof to provide about 0.1-2.0 mg/kg/day or about 0.5-1.0 mg/kg/day or about 2.0 mg/kg/day of isotretinoin. The isotretinoin or pharmaceutically acceptable salt thereof may be provided in an amount of between about 10 mg and about 40 mg, between about 20 mg and about 40 mg, between about 10 mg and about 30 mg, between about 15 mg and about 35 mg, between about 15 mg and about 25 mg, between about 25 mg and about 35 mg, between about 20 mg and about 30 mg, or any combination, sub-combination, range, or sub-range thereof.

The terms "drug" and "pharmaceutical" are used interchangeably to refer to a pharmacologically active substance or composition. These terms of art are well-known in the pharmaceutical and medicinal arts.

The term "excipients" as used herein, refers to any pharmaceutically acceptable materials suitable for the present pharmaceutical preparation and as disclosed herein, which are nontoxic and do not interact with other components of a composition or drug delivery system in a deleterious manner.

The term, "acne" as used herein, refers to skin conditions wherein the skin pore gets blocked and/or thereby becomes inflamed and lead to, including, but not limited to, acneiform or acne-like symptoms characterized by follicular eruptions, comedones, inflamed papules, superficial cysts, and pustules; and deep acne. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, pseudofolliculitis barbae, folliculitis, perioral dermatitis, and hidradenitis suppurativa.

The term "substantially free of" as used herein, refers to a pharmaceutical composition of the present application that has particles of retinoic acid or its derivatives, or isotretinoin or a pharmaceutically acceptable salt thereof, in an amount of less than about 5%, 3%, 2%, 1%, or 0.5% w/w by weight of the present pharmaceutical composition, while formulating or upon storage of the composition.

The term "commercially available isotretinoin composition" refers to ACCUTANE® oral capsules meant for twice daily administration, comprising 10 mg, 20 mg and 40 mg of isotretinoin or its pharmaceutical equivalents or its therapeutic equivalents or later approved drugs which are designated as AB rated by US FDA as per Approved Drug Products with Therapeutic Equivalence Evaluations (34th edition) or drugs having obtained marketing approval by US FDA through Abbreviated New Drug Application (ANDA) filing by establishing bioequivalence to such product. One of the later approved drugs include CLARAVIS' comprising 10 mg, 20 mg, 30 mg and 40 mg of isotretinoin in the form of hard gelatin capsules meant for twice daily oral administration along with excipients such as butylated hydroxyanisole, edetate disodium, gelatin, hydrogenated vegetable oil, polysorbate 80, soybean oil, titanium dioxide, white wax (beeswax), and vitamin E. ACCUTANE® is a Trademark registered and owned by Hoffmann-La Roche Inc. Corporation, 340 Kingsland, N.J. 07110, and CLARAVIS™ is a Trademark registered and owned by Teva Pharmaceuticals USA, Inc. North Wales, Pa. 19454.

The term "amorphous" as used herein, refers to a non-crystalline state of a drug in a pharmaceutical composition. Such amorphous forms generally possess crystal-like short range molecular arrangement, but no long range order of molecular packing as are found in crystalline solids, or as a completely amorphous form within the detection limits of the techniques used for characterization, like powder X-ray diffraction (PXRD), Differential Scanning calorimetry (DSC), by solid state nuclear magnetic resonance (NMR) or any other standard quantitative measurement techniques.

The term "food effect" as used herein refers to food-drug interactions, which refers to all aspects of interactions of food on drug dissolution, absorption, distribution, metabolism, and elimination. The implications of food effect include changes in bioavailability, rate of absorption, duration of therapeutic effect and incidence and seriousness of side effects. This is represented as a ratio of the $AUC_{(0-t/0-\infty)}$ under fed conditions, i.e. $AUC_{(0-t/0-\infty)}$ fed, to the $AUC_{(0-t/0-\infty)}$ under fasted conditions, i.e. $AUC_{(0-t/0-\infty)}$ fast, expressed as, $$\text{Food effect} = AUC_{(0-t/0-\infty)} \text{ fed} / AUC_{(0-t/0-\infty)} \text{ fast}.$$

The terms "without food" or "fasted" as used herein, refers to the condition wherein no food is consumed within at least 1 hour prior to administration of the composition or at least 2 hours after administration of the composition.

In an embodiment, the present application relates to a pharmaceutical composition comprising retinoic acid or its derivatives, wherein at least 60% of said retinoic acid is in an amorphous form.

In an embodiment, the present application relates to a once daily pharmaceutical composition comprising retinoic acid or its derivatives, wherein at least 60% of said retinoic acid is in an amorphous form.

In some embodiments, the "retinoic acid or its derivatives" includes a metabolite of vitamin A (retinol), such as, but not limited to, any naturally occurring or synthetic derivatives, selected from tretinoin, isotretinoin, acitretin, tazarotene, tazarotenic acid, adapalene, and pharmaceutically acceptable salts, esters, isomers, enantiomers, active metabolites, and/or prodrugs thereof. For example, in one embodiment, the retinoic acid or its derivatives includes isotretinoin or a pharmaceutically acceptable salt thereof. In another embodiment, the retinoic acid or its derivatives includes acitretin or a pharmaceutically acceptable salt thereof.

In an embodiment, the present application relates to a pharmaceutical composition comprising isotretinoin or a pharmaceutically acceptable salt thereof, wherein at least 60% of said isotretinoin is in an amorphous form.

In an embodiment, the present application relates to a once daily pharmaceutical composition comprising isotretinoin or a pharmaceutically acceptable salt thereof, wherein at least 60% of said isotretinoin is in an amorphous form.

In an embodiment, the present application relates to a pharmaceutical composition comprising acitretin or a pharmaceutically acceptable salt thereof, wherein at least 60% of said acitretin is in an amorphous form.

In some embodiments, the pharmaceutical composition is substantially free of retinoic acid particles. For example, in one embodiment, the present application relates to a pharmaceutical composition comprising isotretinoin or a pharmaceutically acceptable salt thereof, wherein at least 60% of said isotretinoin is in an amorphous form; and wherein said composition is substantially free of isotretinoin particles. In another embodiment, the present application relates to a pharmaceutical composition comprising acitretin or a pharmaceutically acceptable salt thereof, wherein at least 60% of said acitretin is in an amorphous form; and wherein said composition is substantially free of acitretin particles.

In some embodiments, at least a portion of the retinoic acid in the pharmaceutical composition is in an amorphous form. Suitable amounts of amorphous retinoic acid include, but are not limited to, at least 5%, at least 10%, at least 20%, at least 30%, at least 40%, at least 50%, at least 60%, at least 70%, at least 80%, at least 90%, about 100%, or any combination, sub-combination, range, or sub-range thereof. For example, in one embodiment, at least about 60%, at least about 65%, at least about 70%, at least about 75%, at least about 80%, at least about 85%, at least about 90%, at least about 95%, at least about 98%, or about 100% of the retinoic acid in the pharmaceutical composition is in an amorphous form. In another embodiment, the pharmaceutical composition of the present application includes a mixture of amorphous and crystalline forms of isotretinoin or a pharmaceutically acceptable salt thereof In an aspect of the above embodiments, the pharmaceutical composition of the present application comprising isotretinoin or a pharmaceutically acceptable salt thereof comprises a mixture of amorphous and crystalline forms of said isotretinoin present in a ratio of from about 5:95, 10:90, 20:80, 30:70, 40:60, 50:50, 60:40, 70:30, 80:20, 90:10, 95:5 or 100:0.

In an aspect of the above embodiments, the pharmaceutical composition of the present application comprising isotretinoin or a pharmaceutically acceptable salt thereof comprises at least about 60% of said isotretinoin in an amorphous form, wherein at least about 40% of said isotretinoin is in crystalline form.

In an embodiment, the present application relates to a pharmaceutical composition of retinoic acid comprising:
(i) retinoic acid or its derivatives, and
(ii) at least one solubility improving polymer,
wherein at least 60% of said retinoic acid is in an amorphous form.

In another embodiment, the present application relates to a pharmaceutical composition of isotretinoin comprising:
(i) isotretinoin or a pharmaceutically acceptable salt thereof, and
(ii) at least one solubility improving polymer,
wherein at least 60% of said isotretinoin is in an amorphous form.

In another embodiment, the present application relates to a pharmaceutical composition of acitretin comprising:
(i) acitretin or a pharmaceutically acceptable salt thereof, and
(ii) at least one solubility improving polymer,
wherein at least 60% of said acitretin is in an amorphous form.

In an embodiment, the present application relates to a pharmaceutical composition of retinoic acid comprising:
(i) retinoic acid or its derivatives; and
(ii) at least one solubility improving polymer,
wherein said composition exhibits at least one of the following dissolution profiles when measured in USP type I apparatus at 100 rpm in 900 ml of borate buffer with a pH of 8.0 and at 37° C.:
(a) about 25% to about 40% of retinoic acid in 15 minutes,
(b) about 60% to about 80% of retinoic acid in 30 minutes, and
(c) about 80% to about 99% of retinoic acid in 60 minutes.

In another embodiment, the present application relates to a pharmaceutical composition of isotretinoin comprising:
(i) isotretinoin or a pharmaceutically acceptable salt thereof, and
(ii) at least one solubility improving polymer,
wherein said composition exhibits at least one of the following dissolution profiles when measured in USP type I apparatus at 100 rpm in 900 ml of borate buffer with a pH of 8.0 and at 37° C.:
(a) about 25% to about 40% of isotretinoin in 15 minutes,
(b) about 60% to about 80% of isotretinoin in 30 minutes, and
(c) about 80% to about 99% of isotretinoin in 60 minutes.

In yet another embodiment, the present application relates to a pharmaceutical composition of acitretin comprising:
(i) acitetin or a pharmaceutically acceptable salt thereof, and
(ii) at least one solubility improving polymer, wherein said composition exhibits at least one of the following dissolution profiles when measured in USP type II apparatus at 50 rpm in 900 ml of phosphate buffer with a pH of 7.4 and at 37° C.:
(a) about 45% to about 70% of acitetin in 15 minutes,
(b) about 50% to about 80% of acitetin in 30 minutes, and
(c) about 60% to about 95% of acitetin in 60 minutes.

In an aspect of the above embodiments, the pharmaceutical composition of the present application optionally further comprises at least one rate controlling agent. Rate controlling agent(s) are used in the pharmaceutical composition of the present application, to provide a longer duration of pharmacological response after administration of the dosage form than is ordinarily experienced after administration of a corresponding immediate release composition comprising same drug in the same amount.

In an embodiment, the present application relates to a pharmaceutical composition comprising retinoic acid comprising:
(i) retinoic acid or its derivatives,
(ii) at least one solubility improving polymer, and
(iii) at least one rate controlling agent,
wherein at least 60% of said retinoic acid is in an amorphous form.

In an embodiment, the present application relates to a pharmaceutical composition of isotretinoin comprising:
(i) isotretinoin or a pharmaceutically acceptable salt thereof,
(ii) at least one solubility improving polymer, and
(iii) at least one rate controlling agent,
wherein at least 60% of said isotretinoin is in an amorphous form.

In an embodiment, the present application relates to a pharmaceutical composition of acitretin comprising:
(i) acitretin or a pharmaceutically acceptable salt thereof,
(ii) at least one solubility improving polymer, and
(iii) at least one rate controlling agent, wherein at least 60% of said acitretin is in an amorphous form.

In an embodiment, the present application relates to a once daily pharmaceutical composition of isotretinoin comprising:
(i) isotretinoin or a pharmaceutically acceptable salt thereof,
(ii) at least one solubility improving polymer, and
(iii) at least one rate controlling agent,
wherein at least 60% of said isotretinoin is in an amorphous form.

In an embodiment, the present application relates to a once daily pharmaceutical composition of acitretin comprising:
(i) acitretin or a pharmaceutically acceptable salt thereof,
(ii) at least one solubility improving polymer, and
(iii) at least one rate controlling agent,
wherein at least 60% of said acitretin is in an amorphous form.

In an embodiment, the present application relates to a pharmaceutical composition of retinoic acid comprising:
(i) retinoic acid or its derivatives,
(ii) at least one solubility improving polymer, and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of retinoic acid in 1 hour,
(b) about 10% to about 25% of retinoic acid in 2 hours,
(c) about 25% to about 45% of retinoic acid in 4 hours,
(d) about 45% to about 60% of retinoic acid in 6 hours, and
(e) about 60% to about 80% of retinoic acid in 12 hours.

In another embodiment, the present application relates to a pharmaceutical composition of isotretinoin comprising:
(i) isotretinoin or a pharmaceutically acceptable salt thereof,
(ii) at least one solubility improving polymer, and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours.

In yet another embodiment, the present application relates to a pharmaceutical composition of isotretinoin comprising:
(i) isotretinoin or a pharmaceutically acceptable salt thereof,
(ii) at least one solubility improving polymer, and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours;
wherein at least 60% of said isotretinoin is in an amorphous form.

In yet another embodiment, the present application relates to a once daily pharmaceutical composition of isotretinoin comprising:
(i) isotretinoin or a pharmaceutically acceptable salt thereof,
(ii) at least one solubility improving polymer, and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours.

In yet another embodiment, the present application relates to a once daily pharmaceutical composition of isotretinoin comprising:
(i) isotretinoin or a pharmaceutically acceptable salt thereof,
(ii) at least one solubility improving polymer, and
(iii) at least one rate controlling agent,
wherein said composition exhibits at least one of the following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours;
wherein at least 60% of said isotretinoin is in an amorphous form.

In yet another embodiment, the present application relates to a pharmaceutical composition of retinoic acid comprising:
(i) retinoic acid or its derivatives, and
(ii) at least one solubility improving polymer selected from ionizable polymer, non-ionizable polymer, and mixtures thereof,
wherein at least 60% of said retinoic acid is in an amorphous form.

In yet another embodiment, the present application relates to a pharmaceutical composition of isotretinoin comprising:
(i) isotretinoin or a pharmaceutically acceptable salt thereof, and
(ii) at least one solubility improving polymer selected from ionizable polymer, non-ionizable polymer, and mixtures thereof,
wherein at least 60% of said isotretinoin is in an amorphous form.

In yet another embodiment, the present application relates to a pharmaceutical composition of acitretin comprising:
(i) acitretin or a pharmaceutically acceptable salt thereof, and
(ii) at least one solubility improving polymer selected from ionizable polymer, non-ionizable polymer, and mixtures thereof,
wherein at least 60% of said acitretin is in an amorphous form.

In yet another embodiment, the present application relates to a pharmaceutical composition of isotretinoin comprising:
(i) isotretinoin or a pharmaceutically acceptable salt thereof, and
(ii) at least one solubility improving polymer selected from ionizable polymer,
wherein at least 60% of said isotretinoin is in an amorphous form.

In yet another embodiment, the present application relates to a pharmaceutical composition of isotretinoin comprising:

(i) isotretinoin or a pharmaceutically acceptable salt thereof, and
(ii) at least one solubility improving polymer selected from non-ionizable polymer,
wherein at least 60% of said isotretinoin is in an amorphous form.

In yet another embodiment, the present application relates to a once daily pharmaceutical composition of isotretinoin comprising:
(i) isotretinoin or a pharmaceutically acceptable salt thereof,
(ii) at least one solubility improving polymer selected from ionizable polymer; and
(iii) at least one rate controlling agent,
wherein at least 60% of said isotretinoin is in an amorphous form.

In yet another embodiment, the present application relates to a once daily pharmaceutical composition of isotretinoin comprising:
(i) isotretinoin or a pharmaceutically acceptable salt thereof,
(ii) at least one solubility improving polymer selected from non-ionizable polymer; and
(iii) at least one rate controlling agent,
wherein at least 60% of said isotretinoin is in an amorphous form.

In an aspect of the above embodiments, the pharmaceutical composition of the present application further comprises at least one wetting agent.

In an embodiment, the present application relates to a pharmaceutical composition of retinoic acid comprising:
(i) retinoic acid or its derivatives,
(ii) at least one solubility improving polymer, and
(iii) at least one wetting agent,
wherein at least 60% of said retinoic acid is in an amorphous form.

In an embodiment, the present application relates to a pharmaceutical composition of isotretinoin comprising:
(i) isotretinoin or a pharmaceutically acceptable salt thereof,
(ii) at least one solubility improving polymer, and
(iii) at least one wetting agent,
wherein at least 60% of said isotretinoin is in an amorphous form.

In an embodiment, the present application relates to a pharmaceutical composition of isotretinoin comprising:
(i) isotretinoin or a pharmaceutically acceptable salt thereof,
(ii) at least one solubility improving polymer,
(iii) at least one rate controlling agent, and
(iv) at least one wetting agent,
wherein at least 60% of said isotretinoin is in an amorphous form.

In an embodiment, the present application relates to a once daily pharmaceutical composition of isotretinoin comprising:
(i) isotretinoin or a pharmaceutically acceptable salt thereof,
(ii) at least one solubility improving polymer,
(iii) at least one rate controlling agent, and
(iv) at least one wetting agent,
wherein at least 60% of said isotretinoin is in an amorphous form.

In an embodiment, the present application relates to a once daily pharmaceutical composition of isotretinoin comprising:
(i) isotretinoin or a pharmaceutically acceptable salt thereof,
(ii) at least one solubility improving polymer,
(iii) at least one rate controlling agent, and
(iv) at least one wetting agent,
wherein said composition exhibits at least one of the following dissolution profiles when measured in USP type I apparatus at 100 rpm in 900 ml of borate buffer with a pH of 8.0 at 37° C.:
(a) about 1% to about 10% of retinoic acid in 1 hour,
(b) about 10% to about 25% of retinoic acid in 2 hours,
(c) about 25% to about 45% of retinoic acid in 4 hours,
(d) about 45% to about 60% of retinoic acid in 6 hours, and
(e) about 60% to about 80% of retinoic acid in 12 hours.

In an aspect of the above embodiments, the pharmaceutical composition of the present application comprises at least one solubility improving polymer and isotretinoin present in a weight ratio of not more than about 3.0:1.0.

In another aspect of the above embodiments, the pharmaceutical composition of the present application comprises at least one solubility improving polymer and isotretinoin present in a weight ratio of from about 2.0:1.0 to about 3.0:1.0.

In yet another aspect of the above embodiments, the pharmaceutical composition of the present application comprises at least one solubility improving polymer and isotretinoin present in a weight ratio of about 3.0:1.0, about 2.9:1.0, about 2.7:1.0, about 2.5:1.0, about 2.3:1.0, about 2.1:1.0 or about 2.0:1.0.

In an aspect of the above embodiments, the pharmaceutical composition of the present application comprises at least one solubility improving polymer and at least one wetting agent present in a weight ratio of not more than about 10.0:1.0.

In another aspect of the above embodiments, the pharmaceutical composition of the present application comprises at least one solubility improving polymer and at least one wetting agent present in a weight ratio of from about 10.0:1.0 to about 1.0:1.0.

In yet another aspect of the above embodiments, the pharmaceutical composition of the present application comprises at least one solubility improving polymer and at least one wetting agent present in a weight ratio of about 10.0:1.0, about 9.0:1.0, about 8.0:1.0, about 7.0:1.0, about 6.0:1.0, about 5.0:1.0, about 4.0:1.0, about 3.5:1.0, about 3.0:1.0, about 2.5:1.0, about 2.0:1.0, about 1.5:1.0 or about 1.0:1.0.

In an aspect of the above embodiments, the solubility improving polymers of the present application are selected from the group comprising of ionizable polymer, non-ionizable polymer, and mixtures thereof and comprises from about 10% w/w to about 40% w/w of the composition.

The term "ionizable polymer" as used herein refers to polymers having at least one functional group that is at least about 10% ionized over at least a portion of the physiologically relevant pH range of 1 to 8. The "ionizable polymer" comprises cellulosic and/or non-cellulosic polymers, wherein cellulosic polymers contain ether-linked alkyl carboxy groups, such as carboxy methyl and carboxy ethyl, and ester-linked substituents comprising a carboxylic acid group such as succinate, phthalate, and trimellitate The term "non-ionizable polymer" as used herein refers to cellulosic polymers that possess substantially no ionizable functional groups covalently attached to the polymer. The non-ionizable polymer may contain ionizable functional groups less than about 0.05 or less than about 0.02 milliequivalents per gram of polymer.

Suitable examples of "ionizable cellulosic polymers" include, but not limited to, hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate; mixtures comprising one or more of the foregoing materials.

Suitable examples of "ionizable non-cellulosic polymers" include, but not limited to, carboxylic acid functionalized vinyl polymers such as the carboxylic acid functionalized polymethacrylates and carboxylic acid functionalized polyacrylates, amine-functionalized polyacrylates, and polymethacrylates (e.g. Trade-name: EUDRAGIT® E PO); and carboxylic acid functionalized starches such as starch glycolate.

Suitable examples of "non-ionizable cellulosic polymers" include, but not limited to, hydroxypropyl methyl cellulose acetate, hydroxypropyl methyl cellulose, hydroxypropyl cellulose, methyl cellulose, hydroxyethyl methyl cellulose, hydroxyethyl cellulose acetate, hydroxypropyl cellulose acetate, hydroxyethyl ethyl cellulose; and mixtures comprising one or more of the foregoing materials.

Suitable rate controlling agents that may be used in the present application are selected from the group comprising of pH independent polymers, pH dependent polymers, and mixtures comprising one or more of the foregoing materials. Such rate controlling agents comprise from about 5% w/w to about 20% w/w of the composition.

Suitable examples of pH independent rate controlling agent include polymers selected from, but not limited to, alkylcelluloses such as methylcellulose, ethyl cellulose; hydroxyalkylcelluloses, for example, hydroxypropylcellulose, hydroxypropylmethylcellulose, hydroxyethylcellulose and hydroxymethylcellulose; carboxyalkylcelluloses such as carboxymethylcellulose; alkali metal salts of carboxyalkylcelluloses such as sodium carboxy methylcellulose or mixtures thereof; polyvinyl alcohols that have at least a portion of their repeat units in the unhydrolyzed (vinyl acetate) form (e.g. polyvinyl alcohol-polyvinyl acetate copolymers); polyvinyl pyrrolidinone; polyethylene polyvinyl alcohol copolymers; and polyvinylpyrrolidinone-polyvinyl acetate copolymers; polyalkylene glycols; polyalkylene oxides such as polyethylene oxide and polypropylene oxide and copolymers of ethylene oxide and propylene oxide; polyvinyl acetate dispersion, cellulose acetate, cellulose propionate (lower, medium or higher molecular weight), cellulose acetate propionate, cellulose acetate butyrate; other natural, semi-synthetic, or synthetic polysaccharides such as alginic acid, alkali metal and ammonium salts thereof, carrageenans, galactomannans, tragacanth, agar-agar, gum arabic, guar gum, xanthan gum, starches, pectins, such as sodium carboxymethyl amylopectin, chitin derivates such as chitosan, polyfructans, inulin, sugars, lactose, sucrose, fructose and mannitol; waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil, and mixtures thereof; and combinations comprising one or more of the foregoing materials known to one of ordinary skill in the art.

Suitable examples of pH dependent rate controlling agents include polymers selected from, but not limited to, ammonio methacrylate copolymers type A and B as described in USP, methacrylic acid copolymer type A, B and C as described in USP, polyacrylate dispersion 30% as described in Ph. Eur., cellulose acetate phthalate, cellulose acetate succinate, cellulose triacetate, hydroxypropylmethylcellulose acetate succinate, hydroxypropylmethylcellulose phthalate, hydroxymethylethylcellulose phthalate, carboxymethylethylcellulose phthalate, ethylhydroxyethylcellulose phthalate and the like, acrylic copolymers including, methyl acrylate, acrylic acid copolymer, methyl acrylate, methacrylic acid copolymer, butyl acrylate, methacrylic acid, methyl methacrylate copolymer (e.g. Trade-names: Eudragit L 100 and Eudragit S, available from Rohm Phafma), ethyl acrylate copolymer (e.g. Trade-name: Eudragit L 100-55, available from Rohm Pharma), octyl acrylate copolymer, poly(methyl methacrylate), poly(ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl actylate), poly (octadecyl acrylate). Among these examples, methacrylic acid, methylmethacrylate copolymer, and methacrylic acid, ethylacrylate copolymer are available under the brand name Eudragit®.

The "wetting agent" as used herein refers to a surfactant or a surface active agent or a mixture of such agents that lower the interfacial tension between a solid & a liquid or two liquid. It also provides higher loading efficiency of retinoic acid or its derivatives like isotretinoin for said pharmaceutical composition of the present application. It may be natural or synthetic in origin. Further, it may be non-ionic, anionic, cationic or amphoteric in nature.

Suitable examples of such wetting agents are selected from, but are not limited to, fatty acids, alkyl sulfonates, benzalkonium chloride, dioctyl sodium sulfosuccinate (docusate sodium) and sodium lauryl sulfate (sodium dodecyl sulfate), sorbitan fatty acid esters, Vitamin E TPGS, polyoxyethylene sorbitan fatty acid esters, polyoxyethylene castor oils, hydrogenated castor oils, sodium taurocholic acid, 1-palmitoyl-2-oleoyl-sn-glycero-3-phosphocholine, lecithin, other phospholipids and mono- and diglycerides, polyoxyethylene fatty acid glycerides, stearyl alcohol, cetostearyl alcohol, cholesterol, polyoxyethylene ricin oil, polyethylene glycol glycerides, poloxamers; and mixtures comprising one or more of the forgoing materials. The amount of wetting agents used in the present application may range from about 1% w/w to about 15% w/w of the composition.

In an aspect of the above embodiments, the present application relates to a pharmaceutical composition comprising isotretinoin or a pharmaceutically acceptable salt thereof, wherein at least 60% of said isotretinoin is in an amorphous form. It is generally known that the solubility of amorphous forms is higher compared to the solubility of crystalline forms. In view of this, in some embodiments, at least a major portion of said isotretinoin is in the amorphous form. The term "a major portion" means that at least 60% of the drug is in amorphous form, rather than in a crystalline form. The pharmaceutical composition of the present application composition comprises at least 65%, at least 70%, at least 75%, at least 80%, at least 85%, at least 90%, at least 95% or about 100% of isotretinoin or a pharmaceutically acceptable salt thereof is in amorphous form or said isotretinoin is completely in amorphous form within the detection limits of the techniques used for characterization, like Powder X-ray diffraction (PXRD), Differential Scanning calorimetry (DSC), by solid state nuclear magnetic resonance (NMR) or any other standard quantitative measurement techniques.

The term "immediate release (IR) portion" as used herein, refers to portions of pharmaceutical compositions comprising retinoic acid or its derivatives such as isotretinoin and one more pharmaceutically acceptable excipients, which do not contain any rate controlling agent. The IR portion can be formulated as powder, granules, pellets, mini-tablets, tablets, capsules or caplets.

The term "extended release (ER) portion" as used herein, refers to portions of pharmaceutical compositions comprising retinoic acid or its derivatives such as isotretinoin, at least one pH independent rate controlling agent, and one more pharmaceutically acceptable excipients. The ER portion can be formulated as powder, granules, pellets, mini-tablets, tablets, capsules or caplets, wherein the pH independent rate controlling agents are coated or layered over IR portion or admixed together with isotretinoin and one more pharmaceutically acceptable excipients.

The term "delayed release (DR) portion" as used herein, refers to pharmaceutical compositions comprising retinoic acid or its derivatives such as isotretinoin, at least one pH dependent rate controlling agent, and one or more pharmaceutically acceptable excipients. The DR portion can be formulated as powder, granules, pellets, mini-tablets, tablets, capsules or caplets, wherein the pH dependent rate controlling agents are coated or layered over IR portion. In certain embodiments, the DR portion can be formulated as powder, granules, pellets, mini-tablets, tablets, capsules or caplets, wherein the pH dependent rate controlling agents are coated or layered over ER portion.

In an embodiment, the present application relates to a pharmaceutical composition comprising retinoic acid or its derivatives, and at least one solubility improving polymer, wherein said composition comprises an extended release (ER) portion and/or an immediate release (IR) portion containing retinoic acid with one or more pharmaceutically acceptable excipients; and wherein at least 60% of said retinoic acid is in an amorphous form.

In an embodiment, the present application relates to a pharmaceutical composition comprising retinoic acid or its derivatives, and at least one solubility improving polymer, wherein said composition comprises a delayed release (DR) portion and/or an immediate release (IR) portion, containing retinoic acid with one or more pharmaceutically acceptable excipients; and wherein at least 60% of said retinoic acid is in an amorphous form.

In an embodiment, the present application relates to a pharmaceutical composition comprising retinoic acid or its derivatives, and at least one solubility improving polymer, wherein said composition comprises (i) an extended release (ER) portion and (ii) a delayed release (DR) portion and/or an immediate release (IR) portion, containing retinoic acid with one or more pharmaceutically acceptable excipients; and wherein at least 60% of said retinoic acid is in an amorphous form.

In an embodiment, the present application relates to a pharmaceutical composition comprising retinoic acid or its derivatives, and at least one solubility improving polymer, wherein said composition comprises (i) an extended release (ER) portion and (ii) a delayed release (DR) portion, containing retinoic acid with one or more pharmaceutically acceptable excipients; and wherein at least 60% of said retinoic acid is in an amorphous form.

In an embodiment, the present application relates to a pharmaceutical composition comprising isotretinoin or a pharmaceutically acceptable salt thereof, and at least one solubility improving polymer, wherein said composition comprises an extended release (ER) portion and/or an immediate release (IR) portion, containing isotretinoin with one or more pharmaceutically acceptable excipients; and wherein at least 60% of said isotretinoin is in an amorphous form.

In another embodiment, the present application relates to a pharmaceutical composition comprising isotretinoin or a pharmaceutically acceptable salt thereof, and at least one solubility improving polymer, wherein said composition comprises a delayed release (DR) portion and/or an immediate release (IR) portion, containing isotretinoin with one or more pharmaceutically acceptable excipients; and wherein at least 60% of said isotretinoin is in an amorphous form.

In an embodiment, the present application relates to a pharmaceutical composition comprising isotretinoin or a pharmaceutically acceptable salt thereof, and at least one solubility improving polymer, wherein said composition comprises (i) an extended release (ER) portion and (ii) a delayed release (DR) portion and/or an immediate release (IR) portion, containing isotretinoin with one or more pharmaceutically acceptable excipients; and wherein at least 60% of said isotretinoin is in an amorphous form.

In an embodiment, the present application relates to a pharmaceutical composition comprising isotretinoin or a pharmaceutically acceptable salt thereof, and at least one solubility improving polymer, wherein said composition comprises (i) an extended release (ER) portion and (ii) a delayed release (DR) portion, containing isotretinoin with one or more pharmaceutically acceptable excipients; and wherein at least 60% of said isotretinoin is in an amorphous form.

In another embodiment, the present application relates to a pharmaceutical composition comprising isotretinoin or a pharmaceutically acceptable salt thereof, and at least one solubility improving polymer, wherein said composition comprises (i) about 0 to about 100 percent of isotretinoin in an extended release (ER) portion, (ii) about 0 to about 100 percent of isotretinoin in a delayed release (DR) portion; and/or (iii) about 0 to about 100 percent of isotretinoin in immediate release (IR) portion; and (iv) one or more pharmaceutically acceptable excipients; and wherein at least 60% of said isotretinoin is in an amorphous form.

In yet another embodiment, the present application relates to a pharmaceutical composition comprising isotretinoin or a pharmaceutically acceptable salt thereof, and at least one solubility improving polymer, wherein said composition comprises (i) about 60 to about 80 percent of isotretinoin in an extended release (ER) portion, (ii) about 40 to about 20 percent of isotretinoin in a delayed release (DR) portion and/or an immediate release (IR) portion; and (iii) one or more pharmaceutically acceptable excipients; and wherein at least 60% of said isotretinoin is in an amorphous form.

In an embodiment, present application relates to a once daily pharmaceutical composition of isotretinoin comprising,
(i) isotretinoin or a pharmaceutically acceptable salt thereof,
(ii) at least one solubility improving polymer, and
(iii) at least one rate controlling agent,
wherein said composition comprises (i) about 60 to about 80 percent of isotretinoin in an extended (ER) portion; (ii) about 40 to about 20 percent of isotretinoin in a delayed release (DR) portion and/or an immediate release (IR) portion; and (iii) one or more pharmaceutically acceptable excipients; and said composition exhibits at least one of the following dissolution profiles when measured in USP type I apparatus at 100 rpm in 900 ml of borate buffer with a pH of 8.0 and at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours.

In an embodiment, the present application relates to a once daily pharmaceutical composition of isotretinoin comprising,
(i) isotretinoin or a pharmaceutically acceptable salt thereof,
(ii) at least one solubility improving polymer, and
(iii) at least one rate controlling agent,
wherein said composition comprises (i) about 60 to about 80 percent of isotretinoin in an extended (ER) portion; (ii) about 40 to about 20 percent of isotretinoin in a delayed release (DR) portion; and (iii) one or more pharmaceutically acceptable excipients; and said composition exhibits at least one of the following dissolution profiles when measured in USP type I apparatus at 100 rpm in 900 ml of borate buffer with a pH of 8.0 and at 37° C.:
(a) about 1% to about 10% of isotretinoin in 1 hour,
(b) about 10% to about 25% of isotretinoin in 2 hours,
(c) about 25% to about 45% of isotretinoin in 4 hours,
(d) about 45% to about 60% of isotretinoin in 6 hours, and
(e) about 60% to about 80% of isotretinoin in 12 hours.

In an embodiment, the present application relates to a method of treating acne in a patient in need thereof comprising orally administering to the patient a pharmaceutical composition comprising retinoic acid or its derivatives, wherein at least 60% of said retinoic acid is in an amorphous form.

In an embodiment, the present application relates to a method of treating acne in a patient in need thereof comprising orally administering to the patient a pharmaceutical composition comprising isotretinoin or a pharmaceutically acceptable salt thereof, wherein at least 60% of said isotretinoin is in an amorphous form.

In an embodiment, the present application relates to a method of treating acne in a patient in need thereof comprising orally administering to the patient a pharmaceutical composition comprising acitretin or a pharmaceutically acceptable salt thereof, wherein at least 60% of said acitretin is in an amorphous form.

In an embodiment, the present application relates to a method of treating acne in a patient in need thereof comprising orally administering to the patient a once daily pharmaceutical composition comprising retinoic acid or its derivatives, wherein at least 60% of said retinoic acid is in an amorphous form.

In an embodiment, the present application relates to a method of treating acne in a patient in need thereof comprising orally administering to the patient a once daily pharmaceutical composition comprising isotretinoin or a pharmaceutically acceptable salt thereof, wherein at least 60% of said isotretinoin is in an amorphous form.

In an aspect of the above embodiments, the pharmaceutical composition of the present application comprising isotretinoin or a pharmaceutically acceptable salt thereof comprises a mixture of amorphous and crystalline forms of said isotretinoin present in a ratio of from about 5:95, 10:90, 20:80, 30:70, 40:60, 50:50, 60:40, 70:30, 80:20, 90:10, 95:5 or 100:0.

In an aspect of the above embodiments, the pharmaceutical composition of the present application comprising isotretinoin or a pharmaceutically acceptable salt thereof comprises at least about 60% of said isotretinoin in an amorphous form, wherein at least about 40% of said isotretinoin is in crystalline form.

In an aspect of the above embodiments, the pharmaceutical composition of the present application is administered orally.

In an aspect of the above embodiments, the pharmaceutical composition of the present application is administered orally, as twice-daily.

In an aspect of the above embodiments, the pharmaceutical composition of the present application is administered orally, as once-daily.

In an aspect of the above embodiments, the pharmaceutical composition of the present application is administered to a patient as once-daily or twice-daily or as determined by the physician.

In another aspect of the above embodiments, the pharmaceutical composition of the present application is administered for treating acne in a patient in need thereof as once-daily or twice-daily or as determined by the physician.

In an embodiment, the present application relates to a method of treating acne in a patient in need thereof comprising orally administering to the patient a pharmaceutical composition of retinoic acid or its derivatives comprising:
(i) retinoic acid or its derivatives, and
(ii) at least one solubility improving polymer,
wherein at least 60% of said retinoic acid is in an amorphous form.

In another embodiment, the present application relates to a method of treating acne in a patient in need thereof comprising orally administering to the patient a pharmaceutical composition of isotretinoin comprising:
(i) isotretinoin or a pharmaceutically acceptable salt thereof, and
(ii) at least one solubility improving polymer,
wherein at least 60% of said isotretinoin is in an amorphous form.

In another embodiment, the present application relates to a method of treating acne in a patient in need thereof comprising orally administering to the patient a pharmaceutical composition of acitretin comprising:
(i) acitretin or a pharmaceutically acceptable salt thereof, and
(ii) at least one solubility improving polymer,
wherein at least 60% of said acitretin is in an amorphous form.

In another embodiment, the present application relates to a method of treating acne in a patient in need thereof comprising orally administering to the patient a once daily pharmaceutical composition of retinoic acid or its derivatives comprising:
(i) retinoic acid or its derivatives,
(ii) at least one solubility improving polymer, and
(iii) at least one rate controlling agent, wherein at least 60% of said retinoic acid is in an amorphous form.

In another embodiment, the present application relates to a method of treating acne in a patient in need thereof comprising orally administering to the patient a once daily pharmaceutical composition of isotretinoin comprising:
(i) isotretinoin or a pharmaceutically acceptable salt thereof,
(ii) at least one solubility improving polymer, and
(iii) at least one rate controlling agent,
wherein at least 60% of said isotretinoin is in an amorphous form.

In an aspect of the above embodiments, the method of treating acne comprising orally administering to the patient a pharmaceutical composition of the present application comprises at least one solubility improving polymer and isotretinoin present in a weight ratio of not more than about 3.0:1.0.

In another aspect of the above embodiments, the method of treating acne comprising orally administering to the patient a pharmaceutical composition of the present application comprises at least one solubility improving polymer and isotretinoin present in a weight ratio of from about 2.0:1.0 to about 3.0:1.0.

In yet another aspect of the above embodiments, the method of treating acne comprising orally administering to the patient a pharmaceutical composition of the present application comprises at least one solubility improving polymer and isotretinoin present in a weight ratio of about 3.0:1.0, about 2.9:1.0, about 2.7:1.0, about 2.5:1.0, about 2.3:1.0, about 2.1:1.0 or about 2.0:1.0.

In an aspect of the above embodiments, the present method of treating acne in a patient in need thereof comprising orally administering to the patient a pharmaceutical composition comprising retinoic acid or its derivatives, wherein said composition further comprises at least one wetting agent.

In an aspect of the above embodiments, the present method of treating acne in a patient in need thereof comprising orally administering to the patient a pharmaceutical composition comprising isotretinoin or a pharmaceutically acceptable salt thereof, wherein said composition further comprises at least one wetting agent.

In an aspect of the above embodiments, the present method of treating acne in a patient in need thereof comprising orally administering to the patient a pharmaceutical composition comprising isotretinoin or a pharmaceutically acceptable salt thereof, wherein said composition comprises at least one solubility improving polymer and at least one wetting agent present in a weight ratio of not more than about 10.0:1.0.

In another aspect of the above embodiments, the present method of treating acne in a patient in need thereof comprising orally administering to the patient a pharmaceutical composition comprising isotretinoin or a pharmaceutically acceptable salt thereof, wherein said composition comprises at least one solubility improving polymer and at least one wetting agent present in a weight ratio of from about 10.0:1.0 to about 1.0:1.0.

In another aspect of the above embodiments, the present method of treating acne in a patient in need thereof comprising orally administering to the patient a once daily pharmaceutical composition comprising isotretinoin or a pharmaceutically acceptable salt thereof, wherein said composition comprises at least one solubility improving polymer and at least one wetting agent present in a weight ratio of from about 10.0:1.0 to about 1.0:1.0.

In an aspect of the above embodiments, rate controlling agents that may be used in the present application are selected from the group comprising of pH independent polymers, pH dependent polymers and mixtures comprising one or more of the foregoing materials. Such rate controlling agents comprise from about 5% w/w to about 20% w/w of the composition.

In an embodiment, the present application relates to a method of treating acne in a patient in need thereof comprising orally administering to the patient a pharmaceutical composition of isotretinoin comprising:
(i) isotretinoin or a pharmaceutically acceptable salt thereof,
(ii) at least one solubility enhancing polymer, and
(iii) at least one wetting agent,
wherein at least 60% of said isotretinoin is in an amorphous form.

In another embodiment, the present application relates to a method of treating acne in a patient in need thereof comprising orally administering to the patient a once daily pharmaceutical composition of isotretinoin comprising:
(i) a daily dose of isotretinoin or a pharmaceutically acceptable salt thereof,
(ii) at least one solubility enhancing polymer, and
(iii) at least one rate controlling agent;
wherein said composition upon administration to the patient, exhibits plasma level differences for $AUC_{0-24}$ compared to commercially available twice daily isotretinoin composition that provides the same daily dose.

In yet another embodiment, the present application relates to a method of treating acne in a patient in need thereof comprising orally administering to the patient a once daily pharmaceutical composition of isotretinoin comprising:
(i) a daily dose of isotretinoin or a pharmaceutically acceptable salt thereof,
(ii) at least one solubility enhancing polymer, and
(iii) at least one rate controlling agent;
wherein said composition upon administration to the patient, exhibits at least one of the following plasma level differences for $AUC_{0-24}$ compared to commercially available twice daily isotretinoin composition that provides the same daily dose:
(a) about 5 to about 10% lower between 0 to 5 hours,
(b) about 15 to about 20% higher between 5 to 14 hours; and
(c) about 4 to about 8% lower between 14 to 24 hours.

In an aspect of the above embodiments, the pharmaceutical composition of the present application is administered to a patient in need thereof without regard to food.

In an embodiment, the present application relates to a method of treating acne in a patient in need thereof comprising orally administering to the patient a pharmaceutical composition comprising isotretinoin or a pharmaceutically acceptable salt thereof, wherein said composition has reduced food effect compared to commercially available twice daily isotretinoin.

In another embodiment, the present application relates to a method of treating acne in a patient in need thereof comprising orally administering to the patient a pharmaceutical composition comprising isotretinoin or a pharmaceutically acceptable salt thereof, wherein said composition exhibits at least about 10% less food effect compared to commercially available twice daily isotretinoin composition.

In another embodiment, the present application relates to a method of treating acne in a patient in need thereof comprising orally administering to the patient a pharmaceutical composition comprising isotretinoin or a pharmaceutically acceptable salt thereof, wherein said composition exhibits at least about 25% less food effect compared to commercially available twice daily isotretinoin composition.

In yet another embodiment, the present application relates to a method of treating acne in a patient in need thereof comprising orally administering to the patient a pharmaceutical composition comprising isotretinoin or a pharmaceutically acceptable salt thereof, wherein said composition exhibits at least about 50% less food effect compared to commercially available twice daily isotretinoin composition.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits at least about 5% less or 10% less or 15% less or 20% less or 25% less or 30% less or 35% less or 40% less or 50% less or 55% less or 60% less or 70% less or 80% less or 90% less food effect compared to commercially available twice daily isotretinoin composition.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits less food effect compared to commercially available twice daily isotretinoin composition, and said food effect is less than about 10% in $C_{max}$.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits less food effect compared to commercially available twice daily isotretinoin composition, and said food effect is less than about 10% in AUC ($AUC_{(0-t)}$ and/or $AUC_{(0-\infty)}$).

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits a mean fed/fasted ratio for $AUC_{(0-t)}$ and/or $AUC_{(0-\infty)}$ of less than about 2.0.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits a mean fed/fasted ratio for $AUC_{(0-t)}$ and/or $AUC_{(0-\infty)}$ of less than about 1.5.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits a mean fed/fasted ratio for $AUC_{(0-t)}$ and/or $AUC_{(0-\infty)}$ in the range of about 1.0 to about 2.0.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits a mean fed/fasted ratio for $C_{max}$ of less than about 2.0.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits a mean fed/fasted ratio for $C_{max}$ of less than about 1.5.

In an aspect of above embodiments, the present application relates to a method of treating acne in a patient in need thereof comprising orally administering to the patient a pharmaceutical composition comprising isotretinoin or a pharmaceutically acceptable salt thereof, wherein said composition exhibits a mean fed/fasted ratio for $C_{max}$ in the range of about 1.0 to about 2.0.

In an embodiment, the present application relates to a method of treating acne in a patient in need thereof comprising orally administering to the patient a pharmaceutical composition comprising isotretinoin or a pharmaceutically acceptable salt thereof, wherein said composition when administered once daily to said patient, exhibits bioequivalence to commercially available twice daily isotretinoin composition, and said bioequivalence is established by (a) a 90% Confidence Interval for mean $C_{max}$, which is between 80% and 125%, (b) a 90% Confidence Interval for mean $AUC_{(0-t)}$, which is between 80% and 125% and (c) a 90% Confidence Interval for mean $AUC_{(0-\infty)}$, which is between 80% and 125%.

In an embodiment, the present application relates to a method of treating acne in a patient in need thereof comprising orally administering to the patient a pharmaceutical composition comprising isotretinoin or a pharmaceutically acceptable salt thereof, wherein said composition provides at least about 10% less food effect compared to commercially available isotretinoin composition when administered once daily to said patient, exhibits bioequivalence to commercially available twice daily isotretinoin composition and said bioequivalence is established by (a) a 90% Confidence Interval for mean $C_{max}$, which is between 80% and 125%, (b) a 90% Confidence Interval for mean $AUC_{(0-t)}$, which is between 80% and 125% and (c) a 90% Confidence Interval for mean $AUC_{(0-\infty)}$, which is between 80% and 125%.

In an embodiment, the present application relates to a method of treating acne in a patient in need thereof comprising orally administering to the patient a pharmaceutical composition comprising isotretinoin or a pharmaceutically acceptable salt thereof equivalent to 40 mg of isotretinoin, wherein said composition when administered once daily to said patient under fasting condition, exhibits at least one of the following pharmacokinetic parameters: (a) a $C_{max}$ of about 350.00 ng/ml to about 600.00 ng/ml, (b) an $AUC_{(0-t)}$ of about 5500.00 ng·hr/ml to about 7700.00 ng·hr/ml, and (c) an $AUC_{(0-\infty)}$ ranging from about 5600.00 ng·hr/ml to about 7900.00 ng·hr/ml.

In an embodiment, the present application relates to a method of treating acne in a patient in need thereof comprising orally administering to the patient a pharmaceutical composition comprising isotretinoin or a pharmaceutically acceptable salt thereof equivalent to 40 mg of isotretinoin, wherein said composition when administered once daily to said patient under fed condition, exhibits at least one of the following pharmacokinetic parameters: (a) a $C_{max}$ of about 350.00 ng/ml to about 600.00 ng/ml, (b) an $AUC_{(0-t)}$ of about 6000.00 ng·hr/ml to about 8700.00 ng·hr/ml, and (c) an $AUC_{(0-\infty)}$ ranging from about 6500.00 ng·hr/ml to about 9500.00 ng·hr/ml.

In an aspect of the above embodiments, the once daily pharmaceutical composition of the present application is administered to a patient in an amount of between about 10 mg and about 40 mg, about 10 mg, about 20 mg, about 30 mg, about 40 mg, or any combination, sub-combination, range, or sub-range of said amounts of isotretinoin, to provide daily dose of about 0.1-2.0 mg/kg/day or about 0.5-1.0 mg/kg/day or about 2.0 mg/kg/day of isotretinoin to said patient.

In an aspect of the above embodiments, the once daily pharmaceutical composition of the present application comprises isotretinoin or a pharmaceutically acceptable salt thereof equivalent to an amount of between about 10 mg and about 40 mg, about 10 mg, about 20 mg, about 30 mg, or about 40 mg of isotretinoin, wherein said composition provides daily dose of about 0.1-2.0 mg/kg/day or about 0.5-1.0 mg/kg/day or about 2.0 mg/kg/day of isotretinoin to a patient in need thereof according to the body weight of said patients, as mentioned below:

| Body weight (kg) | Total mg/day | | |
|---|---|---|---|
| | 0.5 mg/day | 1.0 mg/day | 2.0 mg/day |
| 40 | 20 | 40 | 80 |
| 50 | 25 | 50 | 100 |
| 60 | 30 | 60 | 120 |
| 70 | 35 | 70 | 140 |
| 80 | 40 | 80 | 160 |
| 90 | 45 | 90 | 180 |
| 100 | 50 | 100 | 200 |

In another aspect of the above embodiments, the once daily pharmaceutical composition of the present application comprises isotretinoin or a pharmaceutically acceptable salt thereof equivalent to an amount of between about 10 mg and about 40 mg, about 10 mg, about 20 mg, about 30 mg, or about 40 mg of isotretinoin, wherein said composition when administered to a patient provides daily dose of about 0.1-2.0 mg/kg/day or about 0.5-1.0 mg/kg/day or about 2.0 mg/kg/day of isotretinoin to said patient.

In an aspect of the above embodiments, the once daily pharmaceutical composition of the present application comprises isotretinoin or a pharmaceutically acceptable salt thereof equivalent to about 10 mg, about 20 mg, about 30 mg or about 40 mg of isotretinoin, wherein said composition is having dose-proportional pharmacokinetic profile.

In another aspect of the above embodiments, the once daily pharmaceutical composition of the present application comprises isotretinoin or a pharmaceutically acceptable salt thereof equivalent to about 10 mg, about 20 mg, about 30 mg or about 40 mg of isotretinoin, wherein said composition is having dose-proportional $C_{max}$, $AUC_{(0-t)}$ and $AUC_{(0-\infty)}$ values.

The pharmaceutical composition of the present application further comprises pharmaceutically acceptable excipients selected from the group of binders, lubricants, glidants, antiadherents, plasticizers, sweeteners, preservatives, antioxidants, solvents and the like or mixtures thereof.

Suitable examples of binder(s) that may be used in the present application include, but are not limited to, methyl cellulose, hydroxyl propyl cellulose, hydroxyl propyl methyl cellulose, polyvinyl pyrrolidone, polyvinyl alcohol, propylene glycol, pre gelatinized starch, oxide such as polyethylene oxide and the like or mixtures thereof. The binders may be combination of two or more, such as hydroxyl propyl cellulose and hydroxyl propyl methyl cellulose. The binders used in the present application have a viscosity from about 5 centipoise to about 15 centipoise. The amount of binders may range from about 1% w/w to about 10% w/w of the composition.

The lubricant, glidant or anti-tacking agent may be used interchangeably in the composition of the present application and are selected from, but not limited to, metallic stearates such as magnesium stearate, calcium stearate, zinc stearate; stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, colloidal silicon dioxide, magnesium trisilicate, powdered cellulose, starch, tribasic calcium phosphate and the like or mixtures thereof. The amount of such agents may range from about 1% w/w to about 10% w/w of the composition.

The plasticizer used in the composition of the present application provides increase in the flexibility and strength of the composition. Suitable plasticizers may be selected from, but are not limited to, propylene glycol, polyethylene glycol, triethyl citrate, acetyl triethyl citrate, diethyl phthalate, dibutyl phthalate, dibutyl sebacate, tributyl citrate and the like or mixtures thereof. The amount of such plasticizers may range from about 0.1% w/w to about 5% w/w of the composition.

Suitable examples of antioxidants that may be used in the present application include, but are not limited to, butylated hydroxytoluene (BHT), butylated hydroxyanisole (BHA), ascorbic acid, sodium sulfite, sodium meta bisulfite, p-amino benzoic acid, glutathione, propyl gallate and the like or mixtures thereof. The amount of such antioxidants may range from about 0.1% w/w to about 5% w/w of the composition.

Suitable examples of solvents that may be used in the present application include, but are not limited to, organic solvents such as acetone, methyl ethyl ketone, isopropyl alcohol, isopropyl myristate, propylene glycol, ethanol, methanol, dichloromathane; and other aqueous solvents such as water, aqueous polyalkylene glycols containing C1-6 alkyl groups, aqueous carbohydrate solutions; and the like or mixtures thereof.

Other suitable pharmaceutically acceptable excipients that may be used to formulate the present composition are any excipients known to a person skilled in the art and are described in the Handbook of Pharmaceutical Excipients, American Pharmaceutical Association (1986), incorporated herein by reference.

In an aspect of the above embodiments, the present application relates to a process for preparing a pharmaceutical composition comprising retinoic acid or its derivatives such as isotretinoin, wherein said process includes any method known to a person skilled in the art such as, but not limited to, spraying a suspension or dispersion of drug in a conventional coating pan or fluidized bed equipment (such as a Wurster or Glatt) over a carrier substrate by means of solvent evaporation, spray chilling, spray congealing, spray drying, air suspension chilling, air suspension drying; alternatively granulating said drug with carrier substrate; or hot melt extrusion process to prepare drug containing extrudates using suitable extruders like single screw extruder or twin screw extruder, or pelletization; or nanoencapsulation; and any such methods or combinations thereof. Further, the drug loaded carrier substrate or extrudates may be combined with other suitable pharmaceutically acceptable excipients to form a desired dosage form.

In an embodiment, the present application relates to a process for preparing a pharmaceutical composition comprising retinoic acid or its derivatives, wherein said process comprises the steps of (a) dissolving at least one solubility improving polymer with one or more solvents, (b) optionally adding at least one wetting agent to solution of step (a), (c) dissolving the retinoic acid to step (a) or (b), (d) preparing a dispersion mixture by mixing the solution of step (c) with one or more pharmaceutically acceptable excipients, (e) spraying the dispersion of step (d) onto a carrier substrate, (f) converting the retinoic acid loaded particles of step (e) into suitable pharmaceutical dosage form, wherein at least 60% of said retinoic acid is in an amorphous form.

In an embodiment, the present application relates to a process for preparing a pharmaceutical composition comprising isotretinoin or a pharmaceutically acceptable salt thereof, wherein said process comprises the steps of (a) dissolving at least one solubility improving polymer with one or more solvents, (b) optionally adding at least one wetting agent to solution of step (a), (c) dissolving the isotretinoin to step (a) or (b), (d) preparing a dispersion mixture by mixing the solution of step (c) with one or more pharmaceutically acceptable excipients, (e) spraying the dispersion of step (d) onto a carrier substrate, (f) converting the isotretinoin loaded particles of step (e) into suitable pharmaceutical dosage form, wherein at least 60% of said isotretinoin is in an amorphous form.

In an embodiment, the present application relates to a process for preparing a pharmaceutical composition comprising isotretinoin or a pharmaceutically acceptable salt thereof, wherein said process comprises the steps of (a) dissolving at least one solubility improving polymer with one or more solvents, (b) optionally adding at least one wetting agent to solution of step (a), (c) dissolving said isotretinoin to step (a) or (b), (d) preparing a dispersion by mixing the solution of step (c) with one or more pharmaceutically acceptable excipients, (e) spraying the dispersion of step (d) onto a carrier substrate, (f) coating rate controlling polymer solution onto the amorphous isotretinoin loaded particles of step (e), and (g) converting the isotretinoin particles of step (f) into pharmaceutical dosage form, wherein at least 60% of said isotretinoin is in an amorphous form.

In an embodiment, the present application relates to a process for preparing a pharmaceutical composition comprising isotretinoin or a pharmaceutically acceptable salt thereof, wherein said process comprises, (a) dissolving at least one solubility improving polymer with one or more solvents, (b) optionally adding at least one wetting agent to solution of step (a), (c) dissolving said isotretinoin to step (a) or (b), (d) preparing a dispersion mixture by mixing the solution of step (c) with one or more pharmaceutically acceptable excipients, (e) spraying the dispersion of step (d) onto a carrier substrate, (f) converting the isotretinoin loaded particles of step (e) into suitable pharmaceutical dosage form, and (g) coating rate controlling polymer solution onto the dosage form of step (f), wherein at least 60% of said isotretinoin is in an amorphous form.

In an embodiment, the present application relates to a process for preparing a pharmaceutical composition comprising isotretinoin or a pharmaceutically acceptable salt thereof, wherein said process comprises, (a) dissolving at least one solubility improving polymer with one or more solvents, (b) optionally adding at least one wetting agent to solution of step (a), (c) dissolving said isotretinoin to step (a) or (b), (d) preparing a dispersion by mixing the solution of step (c) with one or more pharmaceutically acceptable excipients, (e) spraying the dispersion of step (d) onto a carrier substrate, (f) optionally further coating one or more seal coating polymer solution onto the isotretinoin loaded particles of step (e), (g) optionally further coating rate controlling polymer solution onto the coating of step (f), and (h) converting the isotretinoin particles of step (g) into suitable pharmaceutical dosage form, wherein at least 60% of said isotretinoin is in an amorphous form.

In an embodiment, the present application relates to a process for preparing a pharmaceutical composition comprising isotretinoin or a pharmaceutically acceptable salt thereof, wherein said process comprises, (a) dissolving at least one solubility improving polymer with one or more solvents, (b) optionally adding at least one wetting agent to solution of step (a), (c) dissolving said isotretinoin to step (a) or (b), (d) preparing a dispersion mixture by mixing the solution of step (c) with one or more pharmaceutically acceptable excipients, (e) spray-drying the dispersion of step (d) to remove the solvent and to form a dispersion, (f) converting the dispersion of isotretinoin of step (e) into suitable pharmaceutical dosage form, and (g) coating rate controlling polymer solution onto the dosage form of step (f), wherein at least 60% of said isotretinoin is in an amorphous form.

In an embodiment, the present application relates to a process for preparing a pharmaceutical composition comprising isotretinoin or a pharmaceutically acceptable salt thereof, wherein said process comprises, (a) mixing at least one solubility improving polymer with said isotretinoin and optionally adding at least one wetting agent, (b) processing the mixture of (a) with a hot-melt extrusion process using suitable extruder to form extrudates, (c) optionally coating one or more seal coating polymer solution onto the extrudates of step (b), (d) optionally further coating rate controlling polymer solution onto the extrudates of step (b) or step (c), (e) milling the extrudates of step (b), (f) mixing the milled extrudates of step (b) with one or more pharmaceutically acceptable excipients, (g) converting the blend of step (c), step (d) or step (f) into suitable pharmaceutical dosage form by filling into capsules or compressing into tablets; wherein at least 60% of said isotretinoin is in an amorphous form.

In another embodiment, the present application relates to a process for preparing a pharmaceutical composition comprising acitretin or a pharmaceutically acceptable salt thereof, wherein said process comprises, (a) mixing at least one solubility improving polymer with said acitretin and optionally adding at least one wetting agent, (b) processing the mixture of (a) with a hot-melt extrusion process using suitable extruder to form extrudates, (c) optionally coating one or more seal coating polymer solution onto the extrudates of step (b), (d) optionally further coating rate controlling polymer solution onto the extrudates of step (b) or step (c), (e) milling the extrudates of step (b), (f) mixing the milled extrudates of step (b) with one or more pharmaceutically acceptable excipients, (g) converting the blend of step (c), step (d) or step (f) into suitable pharmaceutical dosage form by filling into capsules or compressing into tablets; wherein at least 60% of said acitretin is in an amorphous form.

In an aspect of the above embodiments, the active ingredient layer comprises isotretinoin or a pharmaceutically acceptable salt thereof, at least one solubility improving polymer, optionally at least one wetting agent and other pharmaceutically acceptable excipients on the carrier substrate. The isotretinoin loaded particles may comprise alternate layers of one or more seal coating polymer layers and one or more rate controlling polymer layers.

All the layers, i.e. drug layer or the polymer layers, may be applied as solution/dispersion of coating ingredients using any conventional technique known in the art such as spray coating in a conventional coating pan or fluidized bed processor or dip coating.

The term "loading efficiency," as used herein refers to the binding affinity of the drug i.e. retinoic acid or its derivatives such as isotretinoin, towards a carrier substrate used during a process of preparing said pharmaceutical composition and can be expressed herein as a percentage.

In an embodiment, the present application relates to a process for preparing a pharmaceutical composition comprising retinoic acid or its derivatives, wherein said process provides loading efficiency for said retinoic acid or its derivatives of at least about 80%.

In another embodiment, the present application relates to a process for preparing a pharmaceutical composition comprising isotretinoin or a pharmaceutically acceptable salt thereof, wherein said process provides loading efficiency for said isotretinoin of at least about 80%.

In an embodiment, the present application relates to a process for preparing a pharmaceutical composition comprising isotretinoin or a pharmaceutically acceptable salt thereof relates to use of carrier substrates, wherein said process provides loading efficiency for said isotretinoin of at least about 80%.

In an embodiment, the present application relates to a process for preparing a pharmaceutical composition comprising isotretinoin or a pharmaceutically acceptable salt thereof relates to use of carrier substrates, wherein said process provides loading efficiency for said isotretinoin of at least about 85%, and wherein at least 60% of said isotretinoin is in an amorphous form.

Suitable carrier substrates that may be used for a process of the present application include, but are not limited to, crystals or sugars or inorganic salts such as crystal lactose, crystalline cellulose and crystal sodium chloride, and spherical granulation products (such as the spherical granulation product of crystalline cellulose (trade name: AVICEL® SP), the spherical granulation product of crystalline cellulose and lactose (Trade name: NONPAREIL® NP-5 and NP-7), the spherical granulation product of refined sucrose (trade name: NONPAREIL®-103); spherical granulation product of lactose and alpha-converted starch; dextrin; dextrose; sucrose; mannitol; maltodextrin; sodium alumino silicate; clays, including bentonite, kaolin, montmorrillonite, attapulgite, halloysite, laponite, and the like; silica, including colloidal silica, mesoporous silica, and fumed silica; zeolites; talc; cholesteramine; polystyrene sulfonates; mono and polysulfonated resins; activated charcoal; and the like or mixtures thereof.

In an aspect of the above embodiments, a process for preparing a pharmaceutical composition of the present application optionally further comprises a seal coating over a drug loaded carrier substrate to protect the drug during handling and ingestion of the dosage form. Suitable examples of polymers that may be used in seal coating in the present application include, but are not limited to, cellulose derivatives like methyl cellulose, carboxy methyl cellulose, hydroxyl propyl cellulose or hydroxyl propyl methyl cellulose; polyethylene glycol, starch and the like or mixtures thereof. The amount of seal coating polymers may range from about 5% to about 20% by weight of the composition.

In an aspect of the above embodiments, a pharmaceutical composition of the present application can be prepared for administering to the patient in need thereof as once daily or twice daily.

In an aspect of the above embodiments, a pharmaceutical composition of the present application comprises solid oral dosage forms.

In an aspect of the above embodiments, a pharmaceutical composition of the present application comprises solid oral dosage forms selected from powder, granules, pellets, mini-tablets, tablets, capsules or caplets.

In an aspect of the above embodiments, a pharmaceutical composition of the present application comprises solid oral dosage forms selected from powders, granules or solid particles; compressed into tablets, filled into sachets, capsules and the like.

The term "capsules" as used herein refers to, any known types of capsule shells which include, but are not limited to hard gelatin, soft gelatin, starch, hydroxyl propyl methyl cellulose hard shell and the like.

In an aspect of the above embodiments, the pharmaceutical composition of the present application is stable and provides chemical and physical stability of retinoic acid or its derivatives in said composition wherein there is no precipitation and no change in assay values, drug release and composition characteristics such as impurities, drug concentration, appearance and the like as disclosed herein, when kept at 40° C./75% relative humidity (RH) and at 25° C./60% RH for 3 to 6 months.

In another aspect of the above embodiments, the pharmaceutical composition of the present application is stable and provides chemical and physical stability of isotretinoin or a pharmaceutically acceptable salt thereof, in said composition wherein there is no precipitation and no change in assay values, drug release and composition characteristics such as impurities, drug concentration, appearance and the like as disclosed herein, when kept at 40° C./75% RH and at 25° C./60% RH for 3 to 6 months.

In another aspect of the above embodiments, the pharmaceutical composition of the present application is stable and provides chemical and physical stability of isotretinoin or a pharmaceutically acceptable salt thereof, in said composition wherein there is no precipitation and no change in assay values, drug release and composition characteristics such as impurities, drug concentration, appearance and the like as disclosed herein, when kept at 40° C./75% RH and at 25° C./60% RH for at least 3 months.

In another aspect of the above embodiments, the pharmaceutical composition of the present application is stable and provides chemical and physical stability of isotretinoin or a pharmaceutically acceptable salt thereof, in said composition wherein there is no precipitation and no change in assay values, drug release and composition characteristics such as impurities, drug concentration, appearance and the like as disclosed herein, when kept at 40° C./75% RH and at 25° C./60% RH for at least 6 months.

In an embodiment, the present pharmaceutical composition of retinoic acid such as isotretinoin can also be co-administered (simultaneously or sequentially) with one or more pharmaceutical agents of value in the form of commercially available dosage forms or which can be developed in a suitable pharmaceutically acceptable dosage forms for treating acne or related disease conditions.

Examples of the pharmaceutical agents that can be co-administered are selected from, but not limited to, systemic and topical antibiotics like tetracycline, minocycline, doxycycline, metronidazole, erythromycin and clindamycin; or commercially available dosage forms of retinoids like tretinoin (vitamin A or retinoic acid) and the like or mixtures thereof.

The present application is further illustrated by the examples which are provided merely to be exemplary of the pharmaceutical composition described above and do not limit the scope of the application. Certain modifications and equivalents will be apparent to those skilled in the art and are intended to be included within the scope of the present application.

The present application is illustrated below by reference to the following examples. However, one skilled in the art will appreciate that the specific methods and results discussed are merely illustrative of the present application, and not to be construed as limiting the application. The following examples may include compilations of data that are representative of data gathered at various times during the course of development and experimentation related to the present application.

EXAMPLES

Example 1

Solubility studies for isotretinoin were carried out using non-aqueous solvents as mentioned in table 1.

TABLE 1

| Solvent | Solubility (mg/ml) |
|---|---|
| Acetone | 30 |
| Methanol | 10 |
| Ethanol | 10 |
| Dichloromethane | 12 |
| Isopropyl alcohol | 12 |

Example 2

Film casting studies were carried out as mentioned below and the results are shown in table 2.

TABLE 2

| | Polymer | |
|---|---|---|
| Reference no. | Name | Observation |
| A | Hypromellose acetate succinate | No crystallization |
| B | Hydroxyl propyl methyl cellulose | No crystallization |
| C | Copolymer of 1-vinyl-2-pyrrolidone and vinyl acetate (Kollidon ® VA 64) | Recrystallization |
| D | Polyvinyl alcohol | Recrystallization |
| E | Dimethyl aminoethyl methacrylate - butyl methacrylate - methyl methacrylate copolymer (Eudragit ® E PO) | No crystallization |
| F | Polyethylene glycol- polyvinyl acetate- polyvinyl caprolactame based graft copolymer (Soluplus ®) | Recrystallization |

Procedure:
1. Polymers, as shown in table 2, were mixed with isotretinoin or a pharmaceutically acceptable salt thereof separately and dissolved in acetone under stirring.
2. Solution prepared in step 1 was casted on a glass plate, and the casted films were observed and analyzed by Powder X-Ray Diffraction (PXRD) patterns for recrystallization of isotretinoin. The PXRD analysis was done by using D8 ADVANCE modular system supplied from Bruker and the results are shown in FIGS. 1-7B.

Examples 3-10

The pharmaceutical compositions comprising isotretinoin or a pharmaceutically acceptable salt thereof may be prepared as given in Table 3.

TABLE 3

| | Quantity per unit (% w/w) | | | | | | | |
|---|---|---|---|---|---|---|---|---|
| Composition | Ex-3 | Ex-4 | Ex-5 | Ex-6 | Ex-7 | Ex-8 | Ex-9 | Ex-10 |
| Drug loading step | | | | | | | | |
| Isotretinoin | 9.00 | 10.81 | 7.75 | 7.75 | 7.75 | 7.75 | 6.9 | 5.01 |
| Sugar spheres | 40.54 | 48.64 | 34.88 | 34.88 | 34.88 | 34.88 | 31.03 | 22.5 |
| Hypromellose acetate succinate | 22.52 | 27.02 | 19.37 | — | — | — | 17.24 | 12.53 |
| Polyvinylpyrrolidinone-polyvinyl acetate copolymers (Kollidon ® VA 64) | — | — | — | 19.37 | — | — | — | — |
| Dimethyl aminoethyl methacrylate-butyl methacrylate-methyl methacrylate copolymer (Eudragit ® E PO) | — | — | — | — | 19.37 | — | — | — |
| Polyvinyl caprolactam-polyvinyl acetate-polyethylene glycol graft copolymer (Soluplus ®) | — | — | — | — | — | 19.37 | — | — |
| Polyoxyl 40 Hydrogenated Castor Oil | 9.00 | 10.81 | 7.75 | 7.75 | 7.75 | 7.75 | 6.9 | 5.01 |
| Talc | 1.80 | 2.16 | 4.84 | 4.84 | 4.84 | 4.84 | 4.31 | 3.13 |
| Edetate disodium | — | — | 0.96 | 0.96 | 0.96 | 0.96 | 86.2 | 0.62 |
| Butylated hydroxyl anisole | — | — | 0.19 | 0.19 | 0.19 | 0.19 | 0.17 | 0.12 |
| Butylated hydroxy toluene | 0.45 | 0.45 | — | — | — | — | — | — |
| Acetone | q.s. | q.s. | q.s. | q.s. | q.s. | q.s. | q.s. | q.s. |
| Water | q.s. | q.s. | q.s. | q.s. | q.s. | q.s. | q.s. | q.s. |
| Coating step-1 | | | | | | | | |
| Hydroxyl propyl methyl cellulose | — | — | 4.73 | 4.73 | 4.73 | 4.73 | 4.21 | 3.06 |
| Polyethylene glycol 400 | — | — | 0.47 | 0.47 | 0.47 | 0.47 | 0.42 | 0.30 |
| Talc | — | — | 2.34 | 2.34 | 2.34 | 2.34 | 2.0 | 1.51 |
| Purified water | — | — | q.s. | q.s. | q.s. | q.s. | q.s. | q.s. |

TABLE 3-continued

| Composition | Ex-3 | Ex-4 | Ex-5 | Ex-6 | Ex-7 | Ex-8 | Ex-9 | Ex-10 |
|---|---|---|---|---|---|---|---|---|
| Coating step-2 | | | | | | | | |
| Ethyl cellulose | 7.43 | — | 9.45 | 9.45 | 9.45 | 9.45 | — | 8.09 |
| Methacrylic Acid - Methyl Methacrylate Copolymer (1:1) (Eudragit ® L 100) | — | — | — | — | — | — | 1.62 | — |
| Methacrylic Acid - Methyl Methacrylate Copolymer (1:2) (Eudragit ® S 100) | — | — | — | — | — | — | 14.58 | — |
| Hydroxyl propyl methyl cellulose | 3.17 | — | 2.36 | 2.36 | 2.36 | 2.36 | — | 5.43 |
| Triethyl citrate | 0.74 | — | 1.18 | 1.18 | 1.18 | 1.18 | 4.82 | 1.32 |
| Talc | 5.31 | — | 3.66 | 3.66 | 3.66 | 3.66 | 4.82 | 3.93 |
| Isopropyl alcohol | q.s. | — | q.s. | q.s. | q.s. | q.s. | q.s. | q.s. |
| water | q.s. | — | q.s. | q.s. | q.s. | q.s. | q.s. | q.s. |
| Coating step-3 | | | | | | | | |
| Hydroxyl propyl methyl cellulose | — | — | — | — | — | — | — | 4.63 |
| Polyethylene glycol 400 | — | — | — | — | — | — | — | 0.46 |
| Talc | — | — | — | — | — | — | — | 2.16 |
| Purified water | — | — | — | — | — | — | — | q.s. |
| Coating step-4 | | | | | | | | |
| Methacrylic Acid - Methyl Methacrylate Copolymer (1:1) (Eudragit ® L 100) | — | — | — | — | — | — | — | 1.25 |
| Methacrylic Acid - Methyl Methacrylate Copolymer (1:2) (Eudragit ® S 100) | — | — | — | — | — | — | — | 11.27 |
| Triethyl citrate | — | — | — | — | — | — | — | 3.75 |
| Talc | — | — | — | — | — | — | — | 3.75 |
| Isopropyl alcohol | — | — | — | — | — | — | — | q.s. |
| water | — | — | — | — | — | — | — | q.s. |
| Total | 100 | 100 | 100 | 100 | 100 | 100 | 100 | 100 |

Procedure:

Examples 3-5

1. Butylated hydroxy toluene/butylated hydroxyl anisole was dissolved in a mixture of water and acetone under stirring.
2. Polyoxyl 40 hydrogenated castor oil was dissolved in solution of step 1 under stirring.
3. Hypromellose acetate succinate was dissolved in solution of step 2 under stirring.
4. Isotretinoin was dissolved in solution of step 3 under stirring.
5. Talc was dispersed in solution of step 4 under stirring.
6. Dispersion of step 5 was layered onto sugar spheres by fluidized bed processor.

Coating Step—1 (Example 5):

7. Hydroxyl propyl methyl cellulose and polyethylene glycol were dissolved in water under stirring.
8. Tal was added in solution of step 7 under stirring.
9. Drug layered sugar spheres of step 6 were coated with dispersion of step 8 using fluidized bed processor.

Coating Step—2 (Example 3, 5 and 9-10):

10. Ethyl cellulose/Methacrylic acid—methyl methacrylate copolymers was dissolved in isopropyl alcohol.
11. Triethyl citrate was added in solution of step 10 under stirring.
12. Hydroxyl propyl methyl cellulose was dissolved in water under stirring.
13. Solution of step 12 was added in solution of step 11 under stirring.
14. Talc was added in dispersion of step 13 under stirring.
15. Drug layered sugar spheres of step 6 or step 9 were coated with dispersion of step 14 using fluidized bed processor.

Coating Step—3 (Example 10):

16. Coating step 1 was repeated.

Coating Step—4 (Example 10):

17. Methacrylic acid—methyl methacrylate copolymers were dissolved in isopropyl alcohol.
18. Triethyl citrate was added in solution of step 17 under stirring.
19. Talc was added in solution of step 18 under stirring.
20. Drug layered sugar spheres of step 9 or step 15 or step 16 were coated with dispersion of step 19 using fluidized bed processor.

Example 3, 5 and 9-10

21. Coated spheres of step 6 or step 15 or step 20 were filled in hard gelatin or hydroxyl propyl methyl cellulose capsules.

Examples 6-8

22. Examples 6-8 were prepared as per example 5 and hypromellose acetate succinate of example 5 was replaced with polyvinylpyrrolidinone-polyvinyl acetate copolymers, dimethyl aminoethyl methacrylate-butyl methacrylate-methyl methacrylate copolymer and polyvinyl caprolactam-polyvinyl acetate-polyethylene glycol graft copolymer for example 6, 7 and 8 respectively.

Examples 11-13

The pharmaceutical compositions comprising acitretin or a pharmaceutically acceptable salt thereof may be prepared as given in Table 4.

TABLE 4

| Composition | Quantity per unit (% w/w) | | |
|---|---|---|---|
| | Ex - 11 | Ex -12 | Ex - 13 |
| Intragranular portion | | | |
| Acitretin | 7.81 | 7.81 | 5.26 |
| Hypromellose acetate succinate | 7.81 | — | — |
| Co-povidone | — | 31.25 | 52.63 |
| Polyoxyl 40 Hydrogenated Castor Oil | 3.12 | 3.12 | 5.26 |
| Total | 18.75 | 42.18 | 63.15 |
| Extragranular portion | | | |
| Microcrystalline cellulose | 80.31 | 56.87 | 9.57 |
| Silicon dioxide | 0.93 | 0.93 | 0.94 |
| Croscarmellose sodium | — | — | 26.31 |
| Total | 100 | 100 | 100 |

Procedure:

1. Acitretin, polyoxyl 40 hydrogenated castor oil and hypromellose acetate succinate/Co-povidone were mixed and co-sifted.
2. Powder blend of step 1 was extruded and milled.
3. The milled extrudates of step 2 were sifted through suitable sieve and mix with microcrystalline cellulose, silicon dioxide and/or croscarmellose sodium.
4. Powder blend of step 3 was filled in hard gelatin or hydroxyl propyl methyl cellulose capsules.

Example 14

The pharmaceutical compositions as prepared in Examples 3-5 and 9-10 were subjected to dissolution studies using USP type I apparatus at 100 rpm in 900 ml of pH 8.0 Borate buffer comprising 0.5% cetrimide and 50 mg/L pancreatin, at 37° C. The results are given in Table 5.

TABLE 5

| Time | % drug dissolved | | | | |
|---|---|---|---|---|---|
| (hour) | Ex - 3 | Ex - 4 | Ex - 5 | Ex - 9 | Ex - 10 |
| 0 | 0 | 0 | 0 | 0 | 0 |
| 0.08 (5 minutes) | 0 | 6 | 0 | 0 | 0 |
| 0.17 (10 minutes) | 0 | 18 | 0 | 0 | 0 |
| 0.25 (15 minutes) | 0 | 32 | 0 | 0 | 0 |
| 0.5 | 0 | 73 | 0 | 0 | 0 |
| 1 | 4 | 89 | 2 | 1 | 1 |
| 2 | 13 | — | 12 | 21 | 15 |
| 4 | 25 | — | 29 | 41 | 40 |
| 6 | 35 | — | 41 | 52 | 52 |
| 8 | 44 | — | 48 | 63 | 61 |
| 12 | 60 | — | 69 | 79 | 73 |
| 16 | — | — | 78 | 87 | 80 |
| 20 | — | — | 84 | 90 | 84 |
| 24 | — | — | 93 | 92 | 87 |

Example 15

The pharmaceutical compositions as prepared in example 9-10 were subjected to change over dissolution studies using USP type I apparatus at 100 rpm, wherein the composition of example 9 was kept in 900 ml fasted simulated intestinal fluid of pH 6.5 for 3 hours, followed by pH 7.4 phosphate buffer comprising 0.5% of tween 80, at 37° C.; and wherein the composition of example 10 was kept in 900 ml fasted simulated intestinal fluid of pH 6.5 for 2 hours, followed by pH 7.4 phosphate buffer comprising 0.5% of tween 80, at 37° C. The results are given in Table 6.

TABLE 6

| Time | % drug dissolved | |
|---|---|---|
| (hour) | Ex - 9 | Ex - 10 |
| 0 | 0 | 0 |
| 1 | 1 | 0 |
| 2 | 11 | 9 |
| 3 | 24 | 39 |
| 4 | 60 | 50 |
| 6 | 77 | 64 |
| 8 | 84 | 73 |
| 10 | 87 | 77 |
| 12 | 89 | 78 |

Example 16

The pharmaceutical compositions as prepared in Examples 11-13 were subjected to dissolution studies using USP type II apparatus at 50 rpm in 900 ml of pH 7.4 Phosphate buffer comprising 0.5% tween 80, at 37° C. The results are given in Table 7.

TABLE 7

| Time | % drug dissolved | | |
|---|---|---|---|
| (minutes) | Ex - 11 | Ex - 12 | Ex - 13 |
| 0 | 0 | 0 | 0 |
| 15 | 52 | 57 | 60 |
| 30 | 60 | 62 | 76 |
| 60 | 65 | 67 | 85 |
| 120 | 68 | 71 | 91 |

Example 17

The pharmaceutical compositions as prepared in Example 3 and Example 5 were subjected to stability studies at 40° C./75% RH, 25° C./60% RH and/or 2-8° C. for 3 to 6 months. The results are given in Table 8 and Table 9.

TABLE 8

Example 3

| Description | Initial | 40° C./75% RH | | | 25° C./60% RH | | |
|---|---|---|---|---|---|---|---|
| | | 1 month | 2 month | 3 month | 1 month | 2 month | 3 month |
| Assay (%) | 100.2 | 102.5 | 102.5 | 106.4 | 97.1 | 106.4 | 109.2 |
| Tretinoin | 0.07 | 0.38 | 0.54 | 0.83 | 0.16 | 0.18 | 0.22 |
| Single highest unknown impurity | 0.02 | 0.08 | 0.11 | 0.14 | 0.09 | 0.09 | 0.09 |
| Total impurities | 0.63 | 1.52 | 1.69 | 2.02 | 1.38 | 1.38 | 1.41 |
| Water by Karl Fischer (%) | 1.88 | 3.36 | 2.34 | — | 2.82 | — | — |
| Dissolution % Release) Time (Hours) | | 900 ml pH 8 borate buffer in USP-I; 100 RPM; 37° C. (% Mean Release) | | | | | |
| 0 | 0 | 0 | 0 | 0 | 0 | 0 | 0 |
| 1 | 5 | 6 | 4 | 5 | 6 | 4 | 5 |
| 4 | 24 | 25 | 21 | 26 | 25 | 21 | 23 |
| 12 | 59 | 70 | 52 | 73 | 64 | 48 | 56 |
| 24 | 84 | 99 | 77 | 102 | 93 | 77 | 94 |

TABLE 9

Example 5

| Description | Initial | 40° C./75% RH | | | 25° C./60% RH | | | 2-8° C. |
|---|---|---|---|---|---|---|---|---|
| | | 1 month | 3 month | 6 month | 1 month | 3 month | 6 month | 3 month |
| Assay (%) | 99.6 | 99.5 | 101.9 | 104.5 | 101.8 | 101.7 | 106 | 101 |
| Tretinoin | 0.11 | 0.19 | 0.15 | 0.22 | 0.1 | 0.06 | 0.08 | 0.03 |
| Single highest unknown impurity | 0.07 | 0.07 | 0.07 | 0.08 | 0.07 | 0.07 | 0.07 | 0.08 |
| Total impurities | 0.36 | 0.43 | 0.45 | 0.54 | 0.31 | 0.29 | 0.3 | 0.28 |
| Water by Karl Fischer (%) | 1.94 | 1.41 | — | 3.28 | 2.64 | 1.99 | 3.05 | 2.26 |
| Dissolution % Release) Time (Hours) | | 900 ml pH 8 borate buffer in USP-I; 100 RPM; 37° C. (% Mean Release) | | | | | | |
| 0 | 0 | 0 | 0 | 0 | 0 | 0 | 0 | 0 |
| 1 | 1 | 1 | 1 | 1 | 1 | 1 | 1 | 1 |
| 4 | 31 | 34 | 36 | 37 | 29 | 29 | 33 | 29 |
| 12 | 73 | 79 | 87 | 94 | 65 | 68 | 83 | 67 |
| 24 | 97 | 98 | 95 | 102 | 87 | 91 | 98 | 91 |

Example 18

The pharmacokinetic parameters for pharmaceutical composition as prepared in Example 5 comprising 40 mg of isotretinoin was studied in comparison with CLARAVIS' (Isotretinoin Capsules USP 20 mg—twice daily) by using open label, three-treatment, three-way randomized crossover fasted and fed study. The study was conducted in 18 adult male healthy subjects in fasting condition (Table 10), and fed condition (Table 11) and the subjects were administered once daily dose of composition of example 5. The results for food effect studies for Example 5 are shown in Table 12.

Figure 9:
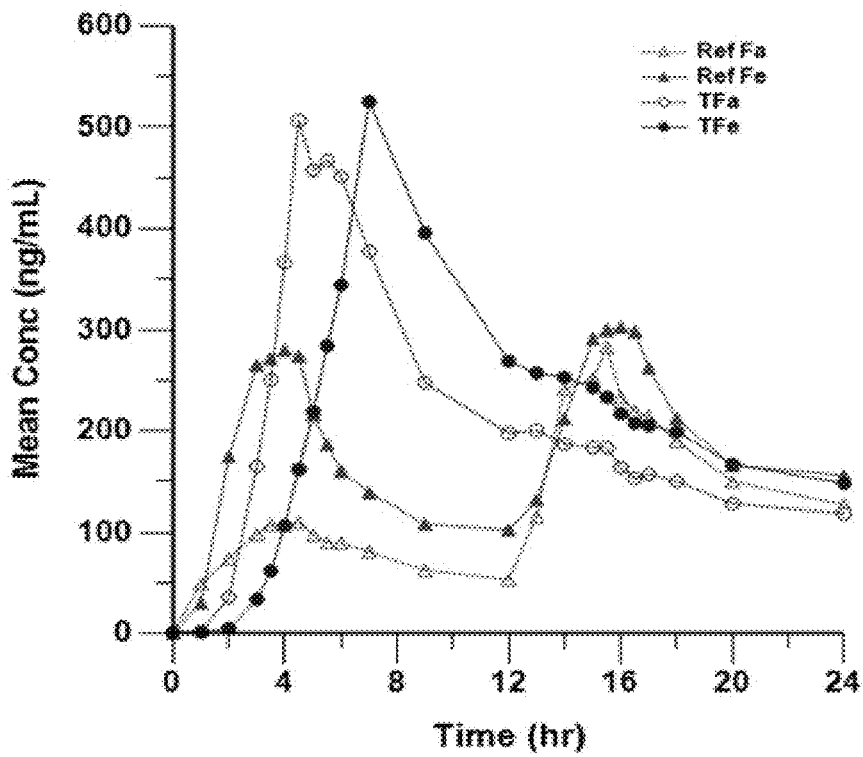
FIG. 9 shows 24 hours mean plasma isotretinoin concentration vs. time profiles for an exemplary composition of the present application, as set forth in Example 5 (T) comprising 40 mg of isotretinoin vis-à-vis 20 mg of twice daily CLARAVIS' (Ref or R) administered to 18 healthy human subjects in fed and fasting conditions.
Figure 10:
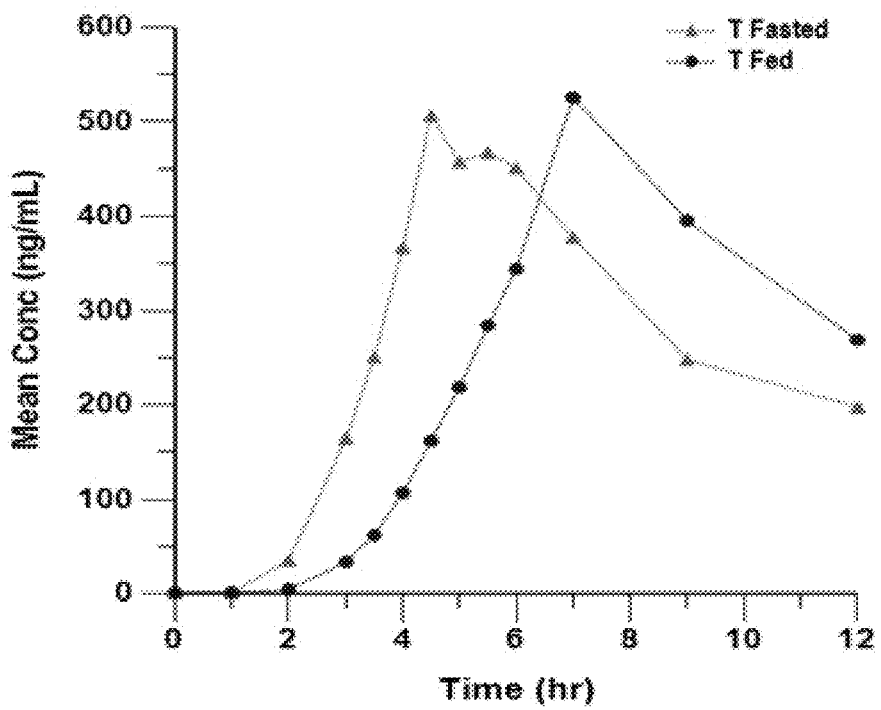
FIG. 10 shows 12 hours mean plasma isotretinoin concentration vs. time profiles for an exemplary composition of the present application, as set forth in Example 5 (T) comprising 40 mg of isotretinoin administered to 18 healthy human subjects in fed vis-à-vis fasting conditions.

The mean plasma isotretinoin concentration vs. time profiles for fed and fasting conditions example 5(T) comprising 40 mg of isotretinoin vis-à-vis 20 mg of twice daily CLARAVIS™ (Ref or R); and fed vis-à-vis fasting conditions for example 5(T) comprising 40 mg of isotretinoin are shown in FIGS. 9 and 10 respectively.

Figure 11:
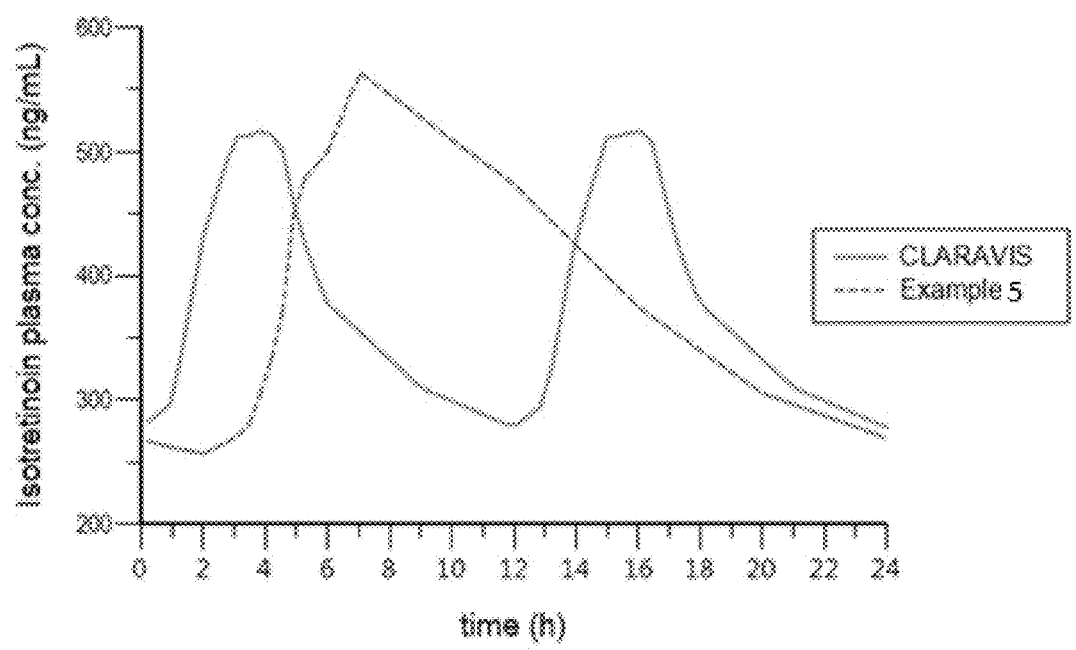
FIG. 11 shows plasma level differences for $AUC_{0-24}$ mean plasma isotretinoin concentration vs. time profiles for an exemplary composition of the present application, as set forth in Example 5 comprising 40 mg of isotretinoin vis-à-vis 20 mg of twice daily CLARAVIS™.

The plasma level differences for $AUC_{0-24}$ showing mean plasma isotretinoin concentration vs. time profiles for an exemplary composition of the present application, as set forth in Example 5 comprising 40 mg of isotretinoin vis-à-vis 20 mg of twice daily CLARAVIS™ were studied and shown in FIG. 11.

TABLE 10

Studies in fasting condition

| Parameters | Ref or R = CLARAVIS ™ | T = Example-5 | % T/R | 90% Confidence Interval - Lower | 90% Confidence Interval - Upper | % CV |
|---|---|---|---|---|---|---|
| $AUC_{(0-t)}$ (hr · ng/ml) | 5550.9 | 6615.9 | 119 | 107 | 133 | 18 |
| $AUC_{(0-\infty)}$ (hr · ng/ml) | 5722.7 | 6821.6 | 119 | 107 | 133 | 18 |
| $C_{max}$ (ng/ml) | 298.8 | 474.8 | 159 | 138 | 182 | 23 |

TABLE 11

Studies in fed condition

| Parameters | Ref or R = CLARAVIS ™ | T = Example-5 | % T/R | 90% Confidence Interval - Lower | 90% Confidence Interval - Upper | % CV |
|---|---|---|---|---|---|---|
| $AUC_{(0-t)}$ (hr · ng/ml) | 7831.4 | 7504.7 | 96 | 91 | 101 | 9 |
| $AUC_{(0-\infty)}$ (hr · ng/ml) | 8258.9 | 7873.7 | 95 | 90 | 101 | 10 |
| $C_{max}$ (ng/ml) | 380.9 | 464.4 | 122 | 109 | 137 | 20 |

TABLE 12

Food effect studies for Example 5

| Parameters | $T_{Fed}$ | $T_{Fast}$ | % $T_{Fe}/T_{Fa}$ | 90% Confidence Interval - Lower | 90% Confidence Interval - Upper | % CV |
|---|---|---|---|---|---|---|
| $AUC_{(0-t)}$ (hr · ng/ml) | 7659.5 | 6621.7 | 116 | 105 | 127 | 16 |
| $AUC_{(0-\infty)}$ (hr · ng/ml) | 7859.5 | 6829.0 | 115 | 105 | 127 | 15 |
| $C_{max}$ (ng/ml) | 506.9 | 477.9 | 106 | 94 | 120 | 21 |

We claim:

1. A once daily solid oral pharmaceutical composition of isotretinoin comprising:
   (a) an extended release (ER) portion comprising
      (i) isotretinoin or a pharmaceutically acceptable salt thereof;
      (ii) a solubility improving polymer comprising from about 10% w/w to about 40% w/w of the composition; and
      (iii) a rate controlling agent comprising from about 5% w/w to about 20% w/w of the composition; and
   (b) an immediate release portion comprising
      (i) isotretinoin or a pharmaceutically acceptable salt thereof;
      (ii) a solubility improving polymer comprising from about 10% w/w to about 40% w/w of the composition;
   wherein said solubility improving polymer and isotretinoin are present in a weight ratio at least about 2.0:1.0;
   wherein said isotretinoin is in an amorphous form and substantially free of crystalline particles; and
   wherein said composition comprises (i) about 60 to about 80 percent of isotretinoin in an extended release (ER) portion, (ii) about 40 to about 20 percent of isotretinoin in an immediate release (IR) portion; and (iii) one or more pharmaceutically acceptable excipients.

2. The composition of claim 1, wherein said solubility improving polymer is selected from ionizable polymer, non-ionizable polymer, and mixtures thereof.

3. The composition of claim 2, wherein said ionizable polymer comprises "cellulosic" and/or "non-cellulosic" polymers.

4. The composition of claim 1, wherein said rate controlling agent is selected from pH independent polymer, pH dependent polymer, and mixtures thereof.

5. The composition of claim 1, wherein said composition further comprises wetting agents.

6. The composition of claim 5, wherein said composition comprises solubility improving polymer and wetting agent present in a weight ratio of not more than about 10.0:1.0.

7. The composition of claim 1, wherein said composition comprises solid oral dosage form selected from powder, granules, pellets, mini-tablets, tablets, capsules or caplets.

8. The composition of claim 1, wherein said composition is stable for at least about 3 months when kept at 40° C./75% Relative Humidity (RH) and at 25° C./60% Relative Humidity (RH).

9. A method of treating acne in a patient in need thereof comprising orally administering to the patient a once daily solid oral pharmaceutical composition of isotretinoin comprising:
   (a) an extended release (ER) portion comprising
      (i) isotretinoin or a pharmaceutically acceptable salt thereof;
      (ii) a solubility improving polymer comprising from about 10% w/w to about 40% w/w of the composition; and (iii) a rate controlling agent comprising from about 5% w/w to about 20% w/w of the composition; and
(b) an immediate release portion comprising
(i) isotretinoin or a pharmaceutically acceptable salt thereof;
(ii) a solubility improving polymer comprising from about 10% w/w to about 40% w/w of the composition;
wherein said solubility improving polymer and isotretinoin are present in a weight ratio at least about 2.0:1.0;
wherein said isotretinoin is in an amorphous form and substantially free of crystalline particles; and
wherein said composition comprises (i) about 60 to about 80 percent of isotretinoin in an extended release (ER) portion, (ii) about 40 to about 20 percent of isotretinoin in a delayed release (DR) portion; and (iii) one or more pharmaceutically acceptable excipients.

10. The method of claim 9, wherein said composition upon administration to the patient under fasting condition, exhibits at least one of the following pharmacokinetic parameters: (a) a $C_{max}$ of about 350.00 ng/ml to about 600.00 ng/ml, (b) an $AUC_{(0-t)}$ of about 5500.00 ng·hr/ml to about 7700.00 ng·hr/ml, and (c) an $AUC_{(0-\infty)}$ ranging from about 5600.00 ng·hr/ml to about 7900.00 ng·hr/ml.

11. The method of claim 9, wherein said composition upon administration to the patient under fed condition, exhibits at least one of the following pharmacokinetic parameters: (a) a $C_{max}$ of about 350.00 ng/ml to about 600.00 ng/ml, (b) an $AUC_{(0-t)}$ of about 6000.00 ng·hr/ml to about 8700.00 ng·hr/ml, and (c) an $AUC_{(0-\infty)}$ ranging from about 6500.00 ng·hr/ml to about 9500.00 ng·hr/ml.

12. The method of claim 9, wherein said once daily composition exhibits at least about 10% less food effect compared to the commercially available twice daily isotretinoin composition.

13. The method of claim 9, wherein said solubility improving polymer is selected from ionizable polymer, non-ionizable polymer and mixtures thereof.

14. The method of claim 13, wherein said ionizable polymer comprises "cellulosic" and/or "non-cellulosic" polymers.

15. The method of claim 9, wherein said composition said rate controlling agent is selected from pH independent polymer, pH dependent polymer and mixtures thereof.

16. The method of claim 9, wherein said composition further comprises at least one wetting agents.

17. The method of claim 16, wherein said composition comprises solubility improving polymer and wetting agent present in a weight ratio of not more than about 10.0:1.0.

18. The method of claim 9, wherein said composition comprises solid oral dosage form selected from powder, granules, pellets, mini-tablets, tablets, capsules or caplets.

19. The composition of claim 1, wherein said composition upon administration exhibits following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours, and
(d) about 60% to about 80% of isotretinoin in 12 hours.

20. A once daily solid oral pharmaceutical composition of isotretinoin comprising: (a) an extended release (ER) portion and (b) a delayed release (DR) portion, wherein said release portions comprises,
(i) isotretinoin or a pharmaceutically acceptable salt thereof;
(ii) a solubility improving polymer comprising from about 10% w/w to about 40% w/w of the composition; and
(iii) a rate controlling agent comprising from about 5% w/w to about 20% w/w of the composition;
wherein said solubility improving polymer and isotretinoin are present in a weight ratio at least about 2.0:1.0;
wherein said isotretinoin is in an amorphous form and substantially free of crystalline particles; and
wherein said composition comprises (i) about 60 to about 80 percent of isotretinoin in an extended release (ER) portion, (ii) about 40 to about 20 percent of isotretinoin in a delayed release (DR) portion; and (iii) one or more pharmaceutically acceptable excipients.

21. The composition of claim 20, wherein said solubility improving polymer is selected from ionizable polymer, non-ionizable polymer, and mixtures thereof.

22. The composition of claim 21, wherein said ionizable polymer comprises "cellulosic" and/or "non-cellulosic" polymers.

23. The composition of claim 20, wherein said rate controlling agent is selected from pH independent polymer, pH dependent polymer, and mixtures thereof.

24. The composition of claim 20, wherein said composition further comprises wetting agents.

25. The composition of claim 24, wherein said composition comprises solubility improving polymer and wetting agent present in a weight ratio of not more than about 10.0:1.0.

26. The composition of claim 20, wherein said composition comprises solid oral dosage form selected from powder, granules, pellets, mini-tablets, tablets, capsules or caplets.

27. The composition of claim 20, wherein said composition is stable for at least about 3 months when kept at 40° C./75% Relative Humidity (RH) and at 25° C./60% Relative Humidity (RH).

28. The composition of claim 20, wherein said composition upon administration exhibits following dissolution profiles when measured in USP type I apparatus at 100 rpm in 900 ml of borate buffer with a pH of 8.0 at 37° C.:
(a) about 1% to about 10% of isotretinoin in 1 hour,
(b) about 10% to about 25% of isotretinoin in 2 hours,
(c) about 25% to about 45% of isotretinoin in 4 hours, and
(d) about 60% to about 80% of isotretinoin in 12 hours.

29. A method of treating acne in a patient in need thereof comprising orally administering to the patient a once daily solid oral pharmaceutical composition of isotretinoin comprising: (i) an extended release (ER) portion and (ii) a delayed release (DR) portion, wherein said release portions comprises,
(i) isotretinoin or a pharmaceutically acceptable salt thereof;
(ii) a solubility improving polymer comprising from about 10% w/w to about 40% w/w of the composition; and
(iii) a rate controlling agent comprising from about 5% w/w to about 20% w/w of the composition;
wherein said solubility improving polymer and isotretinoin are present in a weight ratio at least about 2.0:1.0;
wherein said isotretinoin is in an amorphous form and substantially free of crystalline particles; and
wherein said composition comprises (i) about 60 to about 80 percent of isotretinoin in an extended release (ER) portion, (ii) about 40 to about 20 percent of isotretinoin in a delayed release (DR) portion; and (iii) one or more pharmaceutically acceptable excipients.

Figure 8:
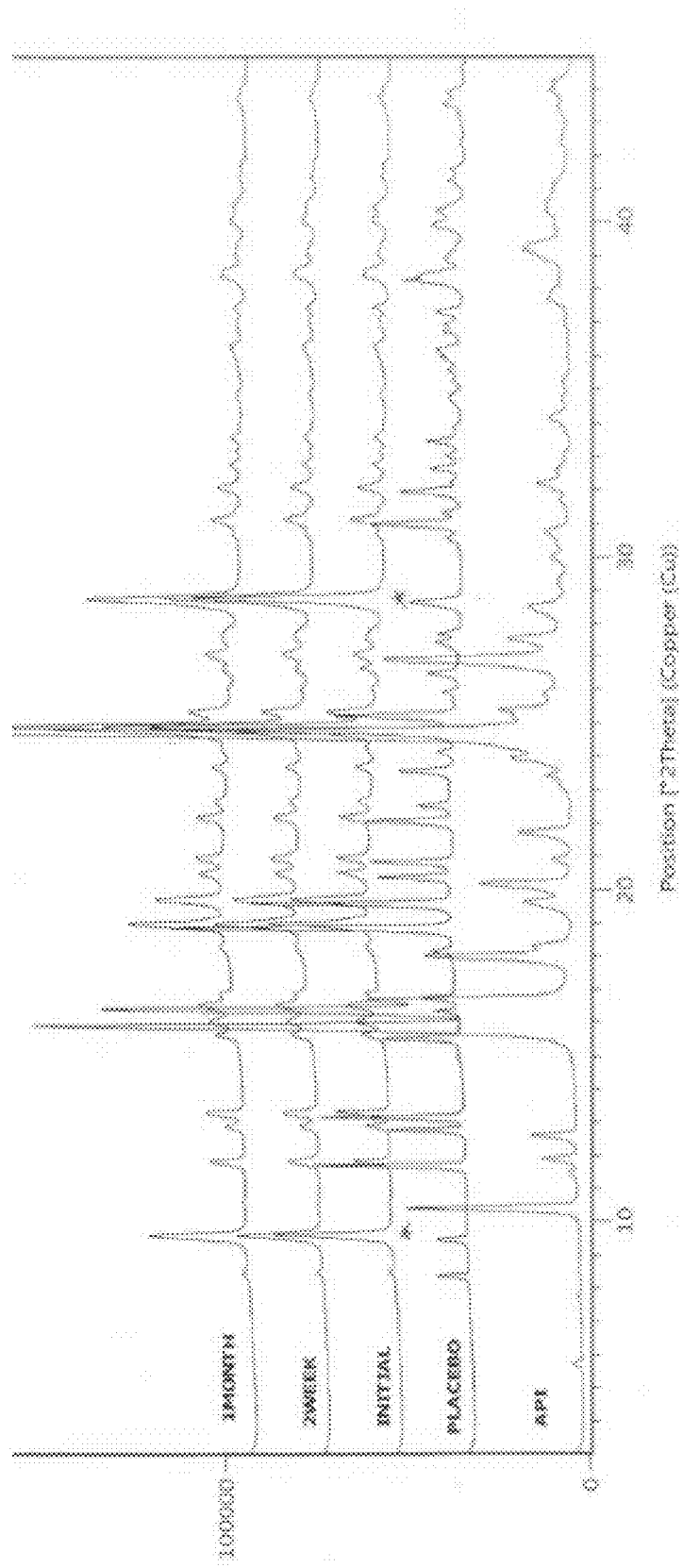
FIG. 8 shows an overlay of Powder X-Ray Diffraction (PXRD) patterns of drug isotretinoin, placebo composition; and an exemplary composition of the present application, as set forth in Example 3, observed at various time periods such as initial, 2 weeks, and 1 month.

30. The composition of claim 1, wherein said isotretinoin is in an amorphous form and has a powder X-ray diffraction (PXRD) as set forth in FIG. 8.

31. The composition of claim 20, wherein said isotretinoin is in an amorphous form and has a powder X-ray diffraction (PXRD) as set forth in FIG. 8.

* * * * *

UNITED STATES PATENT AND TRADEMARK OFFICE
CERTIFICATE OF CORRECTION

PATENT NO. : 10,517,846 B2
APPLICATION NO. : 15/607125
DATED : December 31, 2019
INVENTOR(S) : Yogesh Bapurao Pawar et al.

It is certified that error appears in the above-identified patent and that said Letters Patent is hereby corrected as shown below:

In the Claims

Claim 9, Column 43, Line 3, replace "immediate release portion" with "immediate release (IR) portion"

Claim 16, Column 43, Line 47, replace "comprises at least one wetting agents." with "comprises wetting agents."

Signed and Sealed this
Fourth Day of February, 2020

Andrei Iancu
*Director of the United States Patent and Trademark Office*